US006913056B2

(12) United States Patent
Landherr et al.

(10) Patent No.: US 6,913,056 B2
(45) Date of Patent: Jul. 5, 2005

(54) APPARATUS AND METHOD FOR CONNECTING AND DISCONNECTING FLEXIBLE TUBING

(75) Inventors: Frank J. Landherr, Cary, IL (US); John A. Biewer, Palm Harbor, FL (US); Shahid Din, Clearwater, FL (US); David Do, Valrico, FL (US); Rick Gilbert, Palm Harbor, FL (US); James J. Alberti, St. Petersburg, FL (US); David W. Pennington, Fox Lake, IL (US); Joe Romack, Clearwater, FL (US)

(73) Assignees: Baxter International Inc., Deerfield, IL (US); Baxter Healthcare S.A., Wallisellen (CH)

( * ) Notice: Subject to any disclaimer, the term of this patent is extended or adjusted under 35 U.S.C. 154(b) by 89 days.

(21) Appl. No.: 10/061,835

(22) Filed: Jan. 31, 2002

(65) Prior Publication Data

US 2003/0141009 A1 Jul. 31, 2003

(51) Int. Cl.[7] .............................. B32B 31/20; H05B 1/00
(52) U.S. Cl. ..................... 156/378; 156/379; 156/379.8; 156/380.1; 156/380.9; 156/499; 156/503; 219/243
(58) Field of Search ................................. 156/378, 379, 156/379.6, 379.8, 380.1, 502, 503, 499, 304.2, 304.6; 219/243, 121.6, 121.63–66; 73/52; 29/330, 331; 607/905

(56) References Cited

U.S. PATENT DOCUMENTS

| | | | |
|---|---|---|---|
| 3,063,890 A | 11/1962 | Saumsiegle | |
| 3,542,712 A | 11/1970 | Gorton et al. | |
| 3,645,939 A | 2/1972 | Gaylord et al. | |
| 3,725,174 A | 4/1973 | Gaylord et al. | |
| 3,734,819 A | 5/1973 | Knutson | |
| 3,763,073 A | 10/1973 | Knutson | |
| 3,767,633 A | 10/1973 | Dietrich | |
| 3,956,230 A | 5/1976 | Gaylord | |
| 4,029,850 A | 6/1977 | Ishii et al. | |
| 4,037,020 A | 7/1977 | Ishii et al. | |
| 4,046,728 A | 9/1977 | Harmuth | |
| 4,071,494 A | 1/1978 | Gaylord | |
| 4,089,726 A | 5/1978 | Ishii et al. | |

(Continued)

FOREIGN PATENT DOCUMENTS

| | | |
|---|---|---|
| CA | 1205783 | 6/1986 |
| DE | 3 734 170 | 4/1989 |
| EP | 0 406 485 A | 1/1991 |

(Continued)

OTHER PUBLICATIONS

US 5,693,387, 12/1997, Rosenbaum et al. (withdrawn)
"Infra–Red Welding Technology and Developed Materials For a New Era", by V. Kagan, Honeywell International, presented at Polyamide 2001, The Polyamide chain, Jun. 11–13, 2001.*

(Continued)

Primary Examiner—John T. Haran
(74) Attorney, Agent, or Firm—Joseph P. Reagen; Paula J. Kelly; Bell, Boyd & Lloyd

(57) ABSTRACT

A laser strikes and aseptically heats or sterilizes the end of two flexible tube ends for connection. Tube holders are pushed toward each other to bring the tube ends into contact. A weld detector checks the characteristics of the weld. A laser optics assembly may be used to change the direction of the laser and focus the laser at the tube ends. In addition, a crimping device is used to compress a single flexible tube for disconnection. The laser strikes the compressed area. The crimping device continues to pinch the area and forms a seal in the tube. The tube is separated into two tube segments, each segment has a sealed end.

43 Claims, 14 Drawing Sheets

U.S. PATENT DOCUMENTS

| | | |
|---|---|---|
| 4,126,504 A | 11/1978 | Wolinski et al. |
| 4,210,567 A | 7/1980 | Kosters |
| 4,230,774 A | 10/1980 | Watts et al. |
| 4,316,832 A | 2/1982 | Walkden |
| 4,322,516 A | 3/1982 | Wiest et al. |
| 4,327,726 A | 5/1982 | Kwong et al. |
| 4,369,779 A | 1/1983 | Spencer |
| 4,410,026 A | 10/1983 | Boggs et al. |
| 4,412,835 A | 11/1983 | Spencer |
| 4,417,753 A | 11/1983 | Bacehowski et al. |
| 4,439,192 A | 3/1984 | Leurink |
| 4,488,961 A | 12/1984 | Spencer |
| 4,495,312 A | 1/1985 | Hata et al. |
| 4,496,362 A | 1/1985 | Leurink |
| 4,507,119 A | 3/1985 | Spencer |
| 4,516,971 A | 5/1985 | Spencer |
| 4,516,977 A | 5/1985 | Herbert |
| 4,525,234 A | 6/1985 | Herold et al. |
| 4,587,289 A | 5/1986 | Comert |
| 4,601,948 A | 7/1986 | Lancaster et al. |
| 4,610,670 A | 9/1986 | Spencer |
| 4,619,642 A | 10/1986 | Spencer |
| 4,650,220 A | 3/1987 | Grabowski |
| 4,663,032 A | 5/1987 | Loos et al. |
| 4,664,658 A | 5/1987 | Sawada et al. |
| 4,687,474 A | 8/1987 | Takanashi |
| 4,707,389 A | 11/1987 | Ward |
| 4,720,524 A | 1/1988 | Ohmae et al. |
| 4,723,947 A | 2/1988 | Konopka |
| 4,725,641 A | 2/1988 | Comert et al. |
| 4,726,960 A | 2/1988 | Sawada et al. |
| 4,737,214 A | 4/1988 | Leurink et al. |
| 4,739,012 A | 4/1988 | Hagman |
| 4,740,017 A | 4/1988 | Grabowski |
| 4,753,697 A | 6/1988 | Spencer et al. |
| 4,770,735 A | 9/1988 | Spencer et al. |
| 4,771,106 A | 9/1988 | Ohmae et al. |
| 4,784,409 A | 11/1988 | Piechowiak |
| 4,793,880 A | 12/1988 | Spencer et al. |
| 4,827,099 A | 5/1989 | Krebs et al. |
| 4,832,773 A | 5/1989 | Spencer et al. |
| 4,848,801 A | 7/1989 | Grabowski |
| 4,864,101 A | 9/1989 | Spencer et al. |
| 4,865,902 A | 9/1989 | Golike et al. |
| 4,880,873 A | 11/1989 | Sagane |
| 4,897,138 A | 1/1990 | Spencer et al. |
| 4,900,771 A | 2/1990 | Gerace et al. |
| 4,913,756 A | 4/1990 | Spencer et al. |
| 4,927,184 A | 5/1990 | Bourjot et al. |
| 4,933,036 A | 6/1990 | Spencer et al. |
| 4,948,643 A | 8/1990 | Mueller |
| 4,997,430 A | 3/1991 | Van der Heiden et al. |
| 5,026,019 A | 6/1991 | Biekart et al. |
| 5,037,395 A | 8/1991 | Spencer |
| 5,039,768 A | 8/1991 | Gerace et al. |
| 5,061,451 A | 10/1991 | Ganshirt et al. |
| 5,088,994 A | 2/1992 | Porat et al. |
| 5,135,600 A | 8/1992 | Ishida |
| 5,141,592 A | 8/1992 | Spencer et al. |
| 5,156,701 A | 10/1992 | Spencer et al. |
| 5,158,630 A | 10/1992 | Shaposka et al. |
| 5,166,269 A | 11/1992 | Wietsma et al. |
| 5,179,496 A | 1/1993 | Mimura |
| 5,188,697 A | 2/1993 | Lueghamer et al. |
| 5,209,800 A | 5/1993 | Spencer et al. |
| 5,224,937 A | 7/1993 | van der Heiden et al. |
| 5,244,522 A | 9/1993 | Spencer et al. |
| 5,248,359 A | 9/1993 | Spencer et al. |
| 5,248,562 A | 9/1993 | Palermo et al. |
| 5,250,607 A | 10/1993 | Comert et al. |
| 5,254,825 A | 10/1993 | Schippers |
| 5,256,229 A | 10/1993 | Spencer |
| 5,256,845 A | 10/1993 | Schippers |
| 5,272,304 A | 12/1993 | Been et al. |
| 5,274,035 A | 12/1993 | Chundury |
| 5,279,685 A | 1/1994 | Spencer et al. |
| 5,324,233 A | 6/1994 | Owensby et al. |
| 5,336,351 A | 8/1994 | Meyers |
| 5,342,345 A | 8/1994 | Spencer |
| 5,356,709 A | 10/1994 | Woo et al. |
| 5,367,010 A | 11/1994 | Gervase et al. |
| 5,368,586 A | 11/1994 | Van Der Heiden et al. |
| 5,371,767 A | 12/1994 | Pirl |
| 5,385,979 A | 1/1995 | Ozawa et al. |
| D355,848 S | 2/1995 | Spencer et al. |
| 5,391,610 A | 2/1995 | Comert et al. |
| 5,397,425 A | 3/1995 | Spencer et al. |
| 5,407,742 A | 4/1995 | Tavss et al. |
| 5,410,131 A | 4/1995 | Brunet et al. |
| D357,926 S | 5/1995 | Spencer et al. |
| 5,439,454 A | 8/1995 | Lo et al. |
| 5,460,625 A | 10/1995 | Johnson |
| 5,464,496 A | 11/1995 | Wilson et al. |
| 5,476,718 A | 12/1995 | Ichizuka et al. |
| 5,484,375 A | 1/1996 | Owensby et al. |
| 5,486,210 A | 1/1996 | Kerr et al. |
| 5,492,963 A | 2/1996 | Ozawa et al. |
| 5,496,291 A | 3/1996 | Spencer |
| 5,518,575 A | 5/1996 | Watanabe |
| 5,520,218 A | 5/1996 | Hlavinka et al. |
| 5,525,186 A | 6/1996 | Spencer et al. |
| 5,534,591 A | 7/1996 | Ozawa et al. |
| 5,554,253 A | 9/1996 | Watanabe |
| 5,601,889 A | 2/1997 | Chundury et al. |
| 5,620,738 A | 4/1997 | Fan et al. |
| 5,632,852 A | 5/1997 | Ivansons et al. |
| 5,656,345 A | 8/1997 | Strand et al. |
| 5,674,333 A | 10/1997 | Spencer |
| 5,686,527 A | 11/1997 | Laurin et al. |
| 5,733,268 A | 3/1998 | Spencer |
| 5,749,414 A | 5/1998 | Damsohn et al. |
| 5,802,689 A | 9/1998 | Sano |
| 5,810,792 A | 9/1998 | Fangrow et al. |
| 5,821,293 A | 10/1998 | Roesch et al. |
| 5,824,724 A | 10/1998 | Roesch et al. |
| 5,849,843 A | 12/1998 | Laurin et al. |
| 5,854,347 A | 12/1998 | Laurin et al. |
| 5,855,731 A | 1/1999 | Spencer |
| 5,871,612 A | 2/1999 | Spencer |
| 5,877,236 A | 3/1999 | Roesch et al. |
| 5,879,318 A | 3/1999 | Van Der Heiden et al. |
| 5,919,173 A | 7/1999 | Spencer |
| 5,921,587 A | 7/1999 | Lueghamer |
| 5,922,798 A | 7/1999 | Roesch et al. |
| 5,928,216 A | 7/1999 | Spencer |
| 5,935,847 A | 8/1999 | Smith et al. |
| 5,964,261 A | 10/1999 | Neuenfeldt et al. |
| 5,968,380 A | 10/1999 | Hayashi |
| 5,993,949 A | 11/1999 | Smith et al. |
| 5,998,019 A | 12/1999 | Rosenbaum et al. |
| 6,004,311 A | 12/1999 | Heilmann et al. |
| 6,004,417 A | 12/1999 | Roesch et al. |
| 6,022,344 A | 2/2000 | Meijer |
| 6,024,220 A | 2/2000 | Smith et al. |
| 6,026,882 A | 2/2000 | Yamada et al. |
| 6,071,690 A | 6/2000 | Spencer |
| 6,083,584 A | 7/2000 | Smith et al. |
| 6,094,969 A | 8/2000 | Loos et al. |
| 6,132,833 A | 10/2000 | Spencer |
| 6,149,997 A | 11/2000 | Patel et al. |
| 6,168,862 B1 | 1/2001 | Rosenbaum et al. |

| | | | |
|---|---|---|---|
| 6,201,211 B1 * | 3/2001 | Emmelmann | 219/121.63 |
| 6,225,404 B1 | 5/2001 | Sorensen et al. | |
| 6,251,202 B1 | 6/2001 | Murphy | |
| 6,261,655 B1 | 7/2001 | Rosenbaum et al. | |
| 6,270,599 B1 | 8/2001 | Wood | |
| 6,293,594 B1 | 9/2001 | Safarevich et al. | |
| 6,296,730 B1 | 10/2001 | Williams et al. | |
| 6,297,046 B1 | 10/2001 | Smith et al. | |
| 6,299,596 B1 | 10/2001 | Ding | |
| 6,302,151 B1 | 10/2001 | Maitay | |
| 6,308,882 B1 | 10/2001 | Shuster et al. | |
| 6,333,122 B1 | 12/2001 | Furukawa et al. | |
| 6,368,315 B1 | 4/2002 | Gillis et al. | |
| 6,399,704 B1 | 6/2002 | Laurin et al. | |
| 6,465,068 B1 | 10/2002 | Patel et al. | |
| 6,596,122 B1 * | 7/2003 | Savitski et al. | 156/304.2 |

FOREIGN PATENT DOCUMENTS

| | | |
|---|---|---|
| EP | 0 583 582 A1 | 2/1994 |
| EP | 0 619 175 A2 | 10/1994 |
| EP | 0 508 251 B1 | 8/1995 |
| EP | 0 689 846 A1 | 1/1996 |
| EP | 0 723 851 A2 | 7/1996 |
| EP | 0 725 134 A2 | 8/1996 |
| EP | 0 515 811 B1 | 8/2000 |
| EP | 1 064 960 A2 | 1/2001 |
| JP | 53014772 A | 2/1978 |
| JP | 53014772 A  * | 2/1978 |
| JP | 6-91010 | 4/1994 |
| JP | 6-91011 | 4/1994 |
| JP | 6-233817 | 8/1994 |
| JP | P2000-126288 A | 5/2000 |
| NL | 8 101 391 | 10/1982 |
| WO | WO 8300699 | 3/1983 |
| WO | WO 9315908 A1 | 8/1993 |
| WO | WO 9604704 | 2/1996 |
| WO | WO 200005316 | 2/2000 |
| WO | WO 200146332 A1 | 6/2001 |
| WO | WO 200160586 A1 | 8/2001 |
| WO | WO 2001162314 A2 | 8/2001 |
| WO | WO 200166662 | 9/2001 |
| WO | WO 200185417 | 11/2001 |

OTHER PUBLICATIONS

LaseRevolution, Inc. web page printed Mar. 21, 2001.
Joining Technologies LLC web page, "Electron Beam Welding", printed Mar. 20, 2001.
Ebeam web page printed Mar. 20, 2001.
Dimetrics,Inc. web page printed Mar. 20, 2001.
MPW web page printed Mar. 20, 2001.
Fresenius HemoCare, Inc. web page printed Jun. 6, 2002.
Industrial Microphotonics Company web page printed Mar. 21, 2001.
Joining Technologies web page, "Weld Joint Design", printed Mar. 21, 2001.
Electrox—Manufacturing Solutions web page printed Mar. 21, 2001.
TWI Technology web page printed Mar. 21, 2001.
Joining Technologies, "Laser Beam Welding", printed Mar. 21, 2001.
Copy of web page http://www.cellrobtics.com/perslasette-.html printed on Aug. 3, 2001.
Copy of web page http://www.laserweld.com/laser–welding.html printed Mar. 21, 2001.
Copy of web page http://www.coherentic.com/html/about.html printed Mar. 21, 2001.
Copy of web page www.dencoted.com.

* cited by examiner

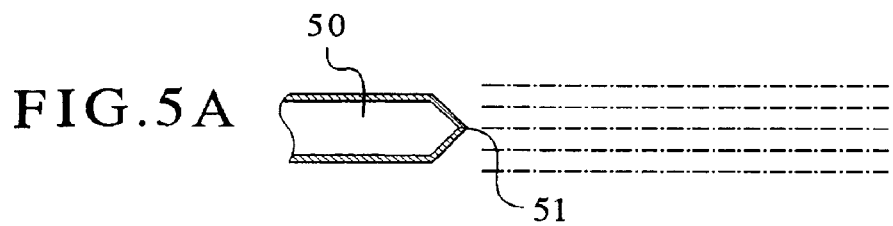
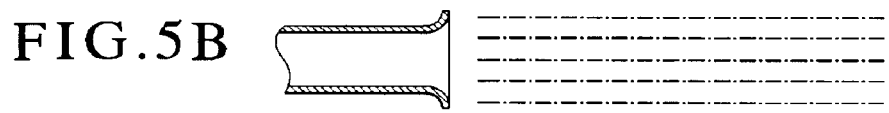
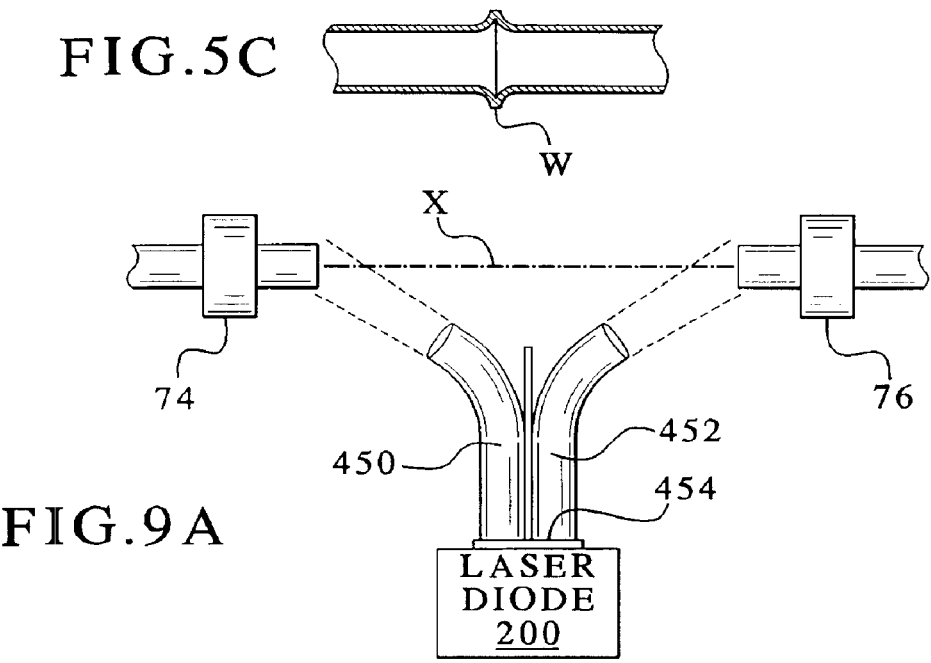
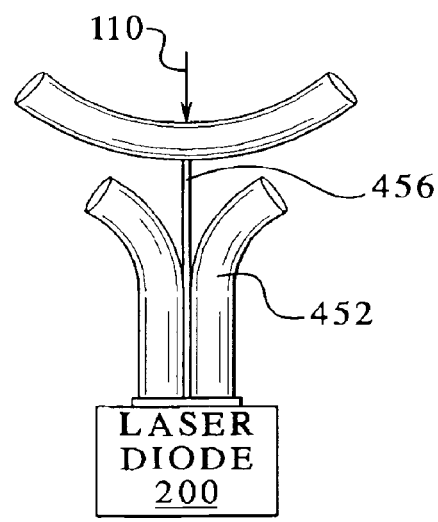

APPARATUS AND METHOD FOR CONNECTING AND DISCONNECTING FLEXIBLE TUBING

BACKGROUND OF THE INVENTION

The present invention relates to the connection and disconnection of the tubing, particularly for tubing used in medical procedures such as dialysis. The present invention also relates to methods for performing such connection and disconnection.

It is known to use medical containers with tubing for various medical procedures. Also, it is known to connect and disconnect patients to and from such tubing.

For example, these tubes are used in systems for treating renal disease. In renal failure of any cause, there are several physiological derangements. The balance of water, minerals and the excretion of daily metabolic load is no longer possible in renal failure. During renal failure, toxic end products of nitrogen metabolism (urea, creatinine, uric acid and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys. Hemodialysis and peritoneal dialysis are two types of dialysis therapies commonly used to treat loss of kidney function.

In general, hemodialysis treatment removes waste, toxins, and excess water from the patient's blood. The patient is connected to a hemodialysis machine and the patient's blood is pumped through the machine. Catheters are inserted into the patient's veins and arteries to connect the blood flow to and from the hemodialysis machine. As blood passes through a dialyzer in the hemodialysis machine, waste, toxins, and excess water are removed from the patient's blood and the blood is infused back into the patient. Many tubes are used in the process that must be connected or disconnected. Hemodialysis treatment lasts several hours and is generally performed in a treatment center about three or four times per week.

Peritoneal dialysis, typically, utilizes a dialysis solution, or dialysate, which is infused into a patient's peritoneal cavity. The dialysate contacts the patient's peritoneal membrane in the peritoneal cavity. Waste, toxins and excess water pass from the patient's bloodstream through the peritoneal membrane and into the dialysate. The transfer of waste, toxins and water from the bloodstream into the dialysate occurs due to diffusion and osmosis, i.e., there is an osmotic gradient across the membrane. The spent dialysate is drained from the patient's peritoneal cavity to remove the waste, toxins and water from the patient. After the spent dialysis is drained, it is replaced with a fresh dialysate solution.

While the present invention has application in connecting or disconnecting tubes for medical procedures, the following discussion focuses, as an example, on a particular tube connection and disconnection performed during peritoneal dialysis. Many tubes are used in the process that must be connected or disconnected. In peritoneal dialysis, the patient has a catheter implanted in the peritoneal cavity and an end protrudes from the patient with a transfer set having a tube for connection or disconnection to fluid bags or discharge bags. Typically, the catheter is made of a silicone material. The transfer set has a spike that connects to a port in the tube for the drain bag or dialysate solution bag. In general, the patient manually stabs the port with the spike to connect the two. The patient connects the tube in the transfer set to a drain to allow spent dialysate fluid to drain from the peritoneal cavity. Next, the patient is connected to a bag of fresh dialysate and manually infuses the fresh dialysate through the catheter and into the patient's peritoneal cavity. When the patient completes treatment, the port is pulled off the spike and a cap is placed on the spike until the patient is ready for the next treatment. When the patient disconnects the catheter from the fresh dialysate bag, the dialysate dwells within the cavity to transfer waste, toxins and excess water from the patient's bloodstream to the dialysate solution. After the dwell period, the patient repeats the manual dialysis procedure and drains the spent dialysate from the peritoneal cavity.

Accordingly, during dialysis treatments such as those described above, the patient is required to connect and disconnect the catheter and transfer set from the fill or drain line (or tube) a number of times. Some devices are available today to assist the patient during the process when using specialized sterilization equipment. However, by and large, these connections/disconnections are performed manually.

One such device, incorporates a heated wafer or hot knife that physically contacts the tubing to cut it by melting the tube and joining two tubes together or melt-sealing the tube ends. Typically, heated wafer applications involve a "melt and wipe" process. In peritoneal dialysis, for example, a patient is ready to drain the spent dialysate or replace his/her peritoneal cavity with fresh dialysate. In this way, the tube extending from the peritoneal cavity has to connect to a tube extending from either a drain bag or a bag containing fresh dialysate. In one "melt and wipe" process, the patient-side tube is bent in a U or V-shape to fit into a U or V-shaped tube holder. Similarly, the bag-side tube is bent in a U or V-shape to fit into another U or V-shaped tube holder. A heated wafer moves across the space between the two tube holders and physically contacts the tubing at the bend junction of the U-shape or V-shape. As the heated wafer contacts the tubing, it melts the tube at the bend junction of the U-shape or V-shape. The wafer then wipes the melted tubing material and removes the material from the area between the tube holders. The two holders are brought together and two connections are made. In the first connection, the patient-side tube is connected to the bag-side tube and the dialysis process is ready to begin. In the second connection, the wasted tube material from the patient-side tube and the bag-side tube is connected together and discarded.

In order to disconnect the patient from the bag, hot knifes are used to cut the tube. An example of a known disconnecting process with the hot knife involves two tubes that are placed side by side across two tube holders. One of the tubes is a short tube having two sealed ends. Generally, the tube holders include a ridge at one end of the tube holder to flatten a portion of the tube to stop fluid flow. The hot knife severs each tube into two pieces. After the hot knife cuts the tube, one of the tube holders moves in relation to the other tube holder. The tubing is "swapped," realigned with one of the cut portions of the short tube, and connected to it—thus, a disconnection is made between the patient and the bag.

These devices have a relatively low level of reliability due to the inconsistency in melting and cutting processes. This inconsistency can result in imperfect seals, leading to leaks, bacterial infiltration and, ultimately, the patient may well experience, among other things, infection or peritonitis.

Also, none of these known methods inspect the integrity of the weld formed between the two tube ends during the connection process. Thus, the user must rely on his/her own visual inspection of the weld.

Moreover, these devices are not user friendly. Often times, patients that need dialysis treatment are visually or otherwise impaired. For example, some dialysis patients experience manual dexterity problems. Many of the known processes involve a great deal of human interaction with loading the tubes into the tube holders. Also, the equipment should be cleaned and the heated wafer replaced after each use to avoid contamination. Thus, making it a difficult process for visually impaired patients and those with poor dexterity.

SUMMARY OF THE INVENTION

The present invention provides improved medical devices and methods of performing medical procedures. In general, the method and device of the present invention include a connecting process and a disconnecting process, each of which use laser technology. In the connecting process, the laser forms a weld between two flexible tubes. In the disconnecting process, the laser seals a tube to form two sealed end tube segments from a single tube.

To this end, in an embodiment of the present invention, a method for providing a connection between two tube ends of flexible material is provided. The method includes the steps of directing a laser beam at the two tube ends and heating each tube end; forcing the heated tube ends together; forming a weld having weld characteristics; and comparing the weld characteristics to a weld profile.

In an embodiment, prior to the step of directing a laser beam at each of the two tube ends, the method further includes the step of determining whether the two tube ends are acceptable for connection together.

In an embodiment, the method further includes the step of confirming that one tube end is a patient-side tube and the other tube end is a bag-side tube.

In an embodiment, the method further includes the step of confirming that one tube end is a patient-side tube and the other tube end is a drain bag-side tube.

In an embodiment, the method further includes the step of using an optics assembly to direct the laser beam.

In an embodiment, the method further includes the step of turning off the laser beam after the tube ends are aseptically heated.

In an embodiment, the method further includes energizing the laser unit to form a weld between the tube ends.

In an embodiment, the method further includes sterilizing the tube ends.

In an embodiment, the method further includes determining whether the weld characteristics are at least equal to the weld profile.

In another embodiment of the present invention, a method for providing a connection between two tube ends of flexible material is provided. The method includes the steps of providing two tube holders, each tube holder receiving one of the two tube ends; directing a laser beam at the two tube ends to sterilize the two tube ends; driving the two tube holders together so that the tube ends contact each other; and forming a weld between the two tube ends.

In an embodiment, the method further includes the steps of guiding each of the two tube ends across the respective tube holder; and stopping each tube end a predetermined distance beyond the tube holder.

In an embodiment, the at least one tube of the two tube ends contains fluid, the method further includes the step of purging fluid from a portion of the at least one tube.

In an embodiment, the method further includes comparing weld characteristics of the weld to a weld profile and determining whether the weld characteristics are at least equal to the weld profile.

In, yet, another embodiment of the invention, a device for providing a connection between two flexible tube ends is provided. The device includes a laser unit that emits a laser beam; a laser optics assembly that is capable of changing a direction of the laser beam so that the laser beam strikes the tube ends; a pair of tube holders, each tube holder is adapted to receive a flexible tube end and to urge the two tube ends together after the tube ends are aseptically heated via the laser beam. The tube holders subsequently join the heated tube ends together to form a weld.

In an embodiment, the laser optics assembly further includes a prism that is movably mounted between the two tube ends.

In an embodiment, the laser optics assembly further includes a prism and a collimator between the laser unit and the prism.

In an embodiment, the laser optics assembly further includes a prism, the prism is not positioned between the pair of tube holders.

In an embodiment, the laser optics assembly further includes a prism and a light pipe, the prism reflects the laser beam to aseptically heat the tube ends and the light pipe directs the laser beam to weld the two tube ends together.

In an embodiment, the laser beam sterilizes the two tube ends.

In an embodiment, the laser optics assembly changes the direction of the laser beam including a plane of the laser beam.

In an embodiment, the weld is a hermetic seal.

In, yet, another embodiment of the present invention, a device is provided for connecting two thermoplastic tube ends together. The device includes two tube holders, each tube holder has an aperture adapted to receive one of the two tube ends; a laser unit in spaced relation to the tube holders, the laser unit projects a laser beam to the two tube ends to sterilize the ends and connect the ends together; and a sensor is near the tube holders, the sensor analyzes the connection between the two tube ends.

In an embodiment, the device further includes a tracking system connected to the two tube holders. The tracking system moves the tube holders together to form a weld between the two tube ends.

In an embodiment, the device further includes an edge detector for sensing the position of each of the two tube ends in the tube holders.

In an embodiment, the device further includes at least one sensor to monitor the temperature near the two tube ends during the connection process.

In an embodiment, the device further includes an optics assembly to direct the laser beam from the laser unit to the tube ends.

In still a further embodiment, a device that provides a sterile connection between two flexible tube ends is provided. The device includes a housing that has a back and two slots, each slot is adapted to receive one of the flexible tube ends; a pair of guides are positioned within the housing near each slot, each of the guides directs one of the flexible tube ends into the housing; a laser unit is positioned near the back of the housing; a pair of tube holders is positioned within the housing, each of the pair of tube holders is adapted to receive the tube end from one of the pair of guides, the tube holders manipulate the flexible tube ends so that each tube end faces the laser unit for heating, bring the heated tube ends together to form a weld, and subsequently release the resulting welded tube.

In an embodiment, the device further including a sensor that corresponds with the guides, the sensor triggers the guides to an "on" state when acceptable tube ends are present in each of the slots.

In an embodiment, the sensor triggers each of the pair of guides to an "off" state when the respective tube end projects a predetermined distance beyond its respective tube holder.

In an embodiment, the pair of guides are pinch rollers.

In an embodiment, the pair of guides are threading devices.

In an embodiment, the laser unit sterilizes the tube ends.

In an embodiment, the laser unit is a semiconductor diode laser.

In an embodiment, the laser unit is a laser diode array.

In an embodiment, the laser unit is an Argon laser.

In an embodiment, the laser unit is a $CO_2$ laser.

In an embodiment, the laser unit is a YAG laser.

In an embodiment, each of the pair of tube holders further include an aperture with a diameter that is slightly smaller than an outer diameter of the flexible tube.

In an embodiment, each tube holder has a tracking system to rotate the tube holder within the housing.

In an embodiment, the pair of tube holders is synchronized and moves simultaneously to manipulate the two flexible tube ends within the housing.

In an embodiment, the device further includes at least one sensor to detect temperature near the tube ends and identify predetermined sterilization levels.

In another embodiment of the present invention, a method for providing a connection between two thermoplastic tubes, each tube having a sealed end, is provided. The method includes the steps of providing a housing adapted to receive the two thermoplastic tubes; providing a laser unit within the housing; loading the sealed end of each thermoplastic tube into the housing; manipulating the thermoplastic tubes within the housing so that each sealed end faces the laser unit; sterilizing and opening the sealed ends by energizing the laser unit; manipulating the thermoplastic tubes again so that the now opened ends are aligned with each other; and welding the two tube ends together via the laser unit.

In an embodiment, the method further includes the step of clamping the thermoplastic tube to prevent flow of fluid near the end of tube.

In an embodiment, the method further includes the steps of receiving each of the thermoplastic tubes in a tube holder; and rotating each tube holder approximately ninety (90) degrees to confront the laser unit.

In an embodiment, the method further includes the step of detecting when the sealed end of each thermoplastic tube approximately faces the laser unit.

In, yet, another embodiment, a method for providing a disconnection of a flexible tube is provided. The method includes the steps of compressing the flexible tube at an area along the tube; striking a laser beam at the compressed area; sealing the compressed area; and separating the flexible tube into two tubes, each tube having a sealed end.

In an embodiment, in which prior to the step of compressing the flexible tube at an area along the tube, the method further includes the step of selecting the area along the flexible tube.

In an embodiment, in which prior to the step of compressing the flexible tube at an area along the tube, the method further includes the step of identifying a weld in the flexible tube; and selecting the area along the flexible tube a predetermined distance from the weld.

In an embodiment, the method further includes the step of pinching the flexible tube between a hammer and an anvil.

In an embodiment, the method further includes the step of directing the laser beam via a light pipe.

In an embodiment, the method further includes the step of forming a hermetic seal.

In an embodiment, the method in which the step of separating the flexible tube into two tubes further includes moving a pair of guides in opposite direction to one another.

In an embodiment, in which prior to the step of separating the flexible tube into two tubes, the method further includes the step of cooling the sealed compressed area.

In still another embodiment of the present invention, a method for providing an aseptic disconnection of a flexible tube is provided. The method includes the steps of providing a housing that has an interior section adapted to receive the flexible tube; providing a laser unit in the interior section of the housing; selecting an area along the flexible tube; crimping the area of the flexible tube; sealing the area via the laser unit; and separating the tube into two tube segments at the area, each of the tube segments having a sealed end.

In another embodiment of the present invention, a device is provided for disconnecting a flexible tube. The device includes a laser unit having an on and off state; a pair of guides, each guide adapted to receive the flexible tube and move the flexible tube; a crimping device in between the pair of guides, the crimping device initially compresses the flexible tube while the laser unit is in the off state, the crimping device further pinches and seals the flexible tube when the laser is in the on state; and the guides move in opposite direction from one another resulting in two sealed segments of flexible tube.

In an embodiment, the two sealed segments are hermetically sealed.

In an embodiment, the device further includes a sensor, the sensor locates a preexisting weld along the flexible tube and the guides move the preexisting weld out of alignment with the crimping device.

In an embodiment, the device further includes a sensor that locates a preexisting weld along the flexible tube and selects an area along the tube, in relation to the preexisting weld, the area being the area of disconnection.

In an embodiment, in which the preexisting weld includes a patient catheter for administering liquid to a patient, the device further includes a sensor that selects the area to be a predetermined distance from the weld along the patient side tube.

In an embodiment, the pair of guides are pinch rollers.

In an embodiment, the pair of guides are threading devices.

In an embodiment, the device further includes a sensor that cooperates with the laser unit, the sensor determines when an acceptable temperature is reached at the selected area.

In an embodiment, the crimping device further includes a hammer and an anvil, the flexible tube is positioned between the hammer and the anvil.

In an embodiment, the anvil is a transparent material.

In an embodiment, the device further includes a light pipe to focus a laser beam of the laser unit to an area along the tube to pinch and seal the tube.

In an embodiment, the laser unit is a semiconductor diode laser.

In an embodiment, the laser unit is an Argon laser.

In an embodiment, the laser unit is a $CO_2$ laser.

In an embodiment, the anvil is automatically replaced after a predetermined number of uses.

In an embodiment, further including a protective film on the anvil.

In an embodiment, the protective film automatically advances after every disconnection of a flexible tube.

In an embodiment, the crimping device includes a hammer and an anvil, the device further includes a film on the anvil in between the hammer and anvil.

In another embodiment of the invention, a device is provided for disconnecting a flexible tube. The device includes a housing having a lid. A hammer and an anvil aligned with the hammer in the housing. The hammer and the anvil compress the flexible tube. A laser unit mounted in the housing, the laser unit is energized after the flexible tube is compressed and de-energized after a seal forms in the compressed tube. A separator that creates a tension at the seal and splits the flexible tube into two tube segments, each tube segment having a sealed end.

In an embodiment, the separator is a pair of guides, the guides are adapted to receive the flexible tube and move in opposite direction to one another.

In still a further embodiment, a device is provided to connect two flexible tube ends together and to disconnect a single flexible tube. The device includes a laser unit having an on and off state, the laser unit emitting a laser beam in the on state; a laser optics assembly capable of changing a direction of the laser beam; a pair of tube holders, each tube holder adapted to receive a flexible tube end, the tube ends being aseptically heated via the laser beam, and the tube holders subsequently join the heated tube ends together to form a weld; a pair of guides, each guide adapted to receive the single flexible tube and move the flexible tube; a crimping device in between the pair of guides, the crimping device initially compresses a flexible tube while the laser unit is in the off state, the crimping device further pinches and seals the flexible tube when the laser is in the on state; and the guides move in opposite direction from one another resulting in two sealed segments of flexible tube.

In, yet another embodiment, a method is provided. The method includes the steps of connecting two flexible tube ends further including striking a laser beam at each of the two tube ends and sterilizing each tube end, forcing the sterilized tube ends together, forming a weld, the weld having weld characteristics, and comparing the weld characteristics to a weld profile; and disconnecting a flexible tube further including compressing the flexible tube at an area along the tube, striking the laser beam at the compressed area, sealing the compressed area, and separating the flexible tube into two tube segments, each tube segment having a sealed end.

In still a further embodiment, a method of providing dialysis treatment to a patient is provided. The method includes the step of sealing a first tube end and a second tube end of medical tubing together via a laser unit.

In another embodiment a method of disconnecting a patient from dialysis treatment is provided. The method includes the steps of crimping and separating a medical tubing into two tube segments via a laser unit.

In, yet another embodiment, device that provides a connection between two flexible tube ends is provided. The device includes a laser unit having a laser beam; a pair of tube holders each adapted to receive a flexible tube end and adapted to urge the two tube ends together after the two tube ends are heated via the laser beam, to join the heated tube ends together to form a weld; and a prism that is not positioned between the pair of tube holders, the prism is capable of changing a direction of the laser beam so that the laser beam strikes the tube ends.

In another embodiment, a device to connect two flexible tube ends and to disconnect a single flexible tube is provided. The device includes a laser unit having an on and off state, the laser unit emits a laser beam in the on state. A laser optics assembly capable of changing a direction of the laser beam. A film covering a surface of the laser optics assembly, the film is capable of advancing after each connection and disconnection. A pair of tube holders, each tube holder adapted to receive a flexible tube end, the tube ends being aseptically heated via the laser beam, and the tube holders subsequently join the heated tube ends together to form a weld. A pair of guides, each guide adapted to receive the single flexible tube and move the flexible tube. A crimping device in between the pair of guides, the crimping device initially compresses a flexible tube while the laser unit is in the off state, the crimping device further pinches and seals the flexible tube when the laser is in the on state; and the guides move in opposite direction from one another resulting in two sealed segments of flexible tube.

An advantage of the present invention is that it provides a unique device and method for connecting two originally sealed ends of flexible tubes.

Another advantage of the present invention is that it provides a device and method that aseptically connects two tube ends.

Another advantage of the present invention is that it provides a device and method that provides a sterile connection between two tube ends.

Another advantage of the present invention is that it provides a device and method for connecting a patient to a dialysis treatment.

Another advantage of the present invention is that it provides a unique device and method to disconnect and seal a flexible tube.

Another advantage of the present invention is that it provides a device and method that provides an aseptic disconnection of a flexible tube.

Another advantage of the present invention is that it provides a device and method that provides a sterile disconnection of a flexible tube.

Another advantage of the present invention is that it provides a device and method for disconnecting a patient from dialysis treatment.

Another advantage of the present invention is that the device and method provide a sterile disconnection of a single tube.

Another advantage of the present invention is that the device and method are compatible with various dialysis therapies.

Yet, another advantage of the present invention is that it provides a device and method that can fully automate aseptically the process of loading and unloading connected or disconnected tubing to limit user touch contamination.

Another advantage of the present invention is that it provides a device and method that simplify the process of making and breaking sterile tubing connections for visually impaired users.

Another advantage of the present invention is that it provides a device and method that reduce wastage of the patient's transfer set during the disconnection process.

A still further advantage of the present invention is that it minimizes human error associated with improper loading of tubes into the device.

Another advantage of the present invention is that it provides a device and method that monitor the tubing temperature during the connection and disconnection of the tubing.

Another advantage of the present invention is that it provides a device and method that inspect the integrity of a weld formed between two tubes during the connection process.

A still further advantage of the present invention is that it provides a device and method that compare the characteristics of the weld formed between two tubes with a weld profile.

Another advantage of the present invention is that it reduces the need to clean the machine after each use.

Another advantage of the present invention is that the device is small and compact.

Additional features and advantages of the present invention are described in, and will be apparent from, the following Detailed Description of the Invention and the figures.

BRIEF DESCRIPTION OF THE FIGURES

FIGS. 5A through 5C illustrate a schematic cross-section view of an embodiment of a sealed end tube of the present invention.

FIGS. 9A and 9B illustrate a schematic plan view of another embodiment of the present invention.

DETAILED DESCRIPTION OF THE INVENTION

Although the present invention can be made in many different forms, the presently preferred embodiments are described in this disclosure and shown in the attached drawings. This disclosure exemplifies the principles of the present invention and does not limit the broad aspects of the invention only to the illustrated embodiments.

Generally, the present invention relates to the aseptic connection and disconnection of tubing. Such tubing can be advantageously used to transfer fluid or blood to and from the human body. In a preferred embodiment, the present invention pertains to a device that opens sealed tube ends and connects the opened tube ends together. Moreover, the device disconnects a tube and reseals the tubing. All of these processes use laser generated heat and provide a connection or disconnection that is aseptic or sterile.

The Device

Figure 1:
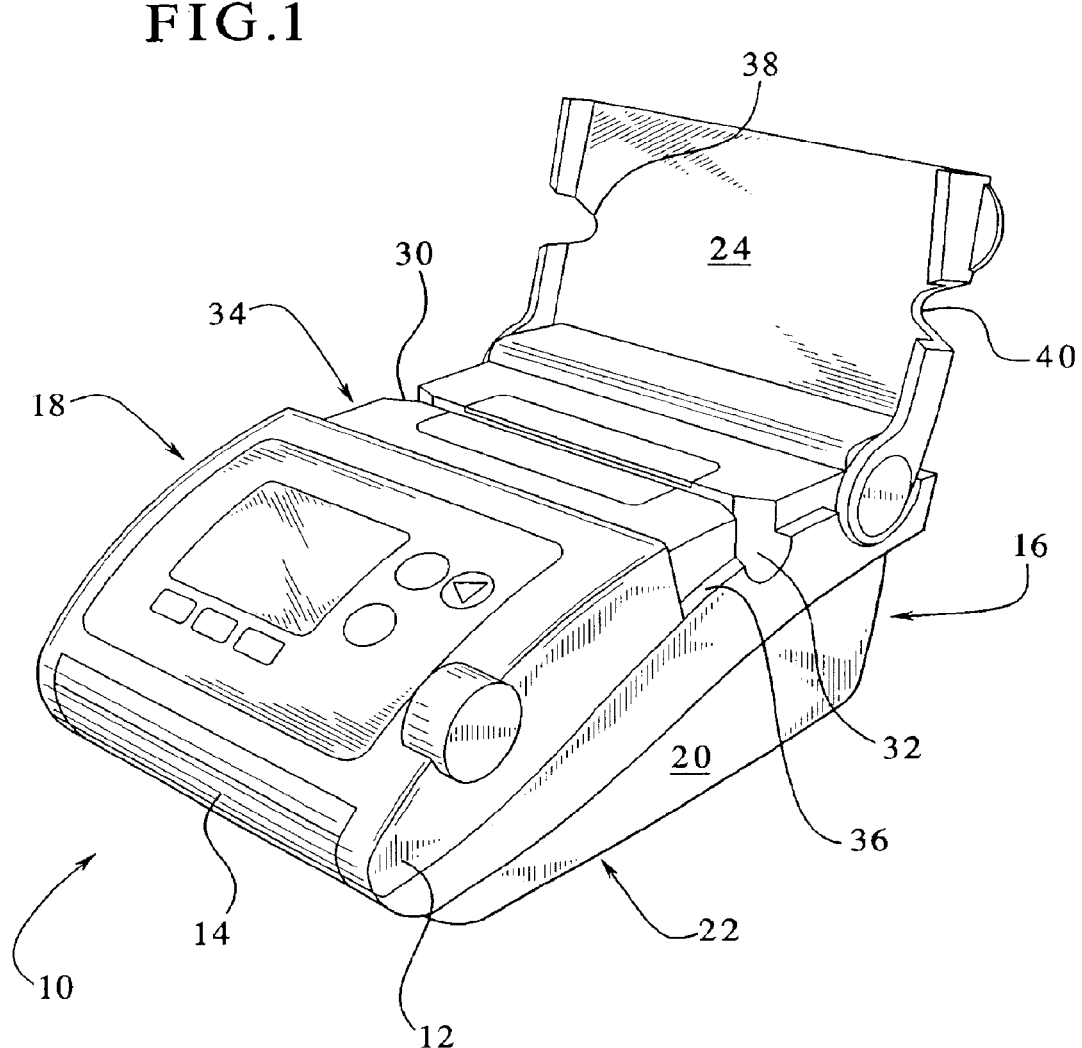
FIG. 1 illustrates a perspective view of a housing of an embodiment of the present invention.

FIG. 1 shows a device 10 according to an embodiment of the present invention. The device 10 includes a housing 12 that has a front 14, a back 16, and two sides 18, 20 there between. The housing 12 also includes a bottom 22 and a lid or door 24. The four sides 14, 16, 18, 20 and bottom 22 define an interior area A. Two slots or openings 30, 32 are located at upper ends 34, 36 of two sides 18, 20 of the housing 12. The door 24 is hinged to the back 16 of the housing 12. The door 24 may be hinged in any number of ways to allow it to be easily opened and shut. The door includes a locking mechanism (not shown) to lock the door closed when the device is in operation. In an embodiment, the door 24 also has two slots 38, 40 that align with the slots 30, 32 to create an area (not shown) for loading and unloading tubing 50 which will be described in further detail below.

FIGS. 2A through 2D show the inside of the device 10 according to an embodiment of the present invention. Inside the housing 12 are two passageways 52, 54. In an embodiment, the passageways 52, 54 are funneled. Each passageway leads to a guide 56, 58. The guides 56, 58 receive the tubing 50 and advance the tubing 50 within the housing 12. The guides are, preferably, pinch rollers, however, various types of guides or threading devices, may be used. In a preferred embodiment, the guides 56, 58 crimp the tubing 50 as it is fed into the device 10. (See FIG. 2A, Ref. No. 58). This crimping purges fluid from a portion 60 of the tube 50 that progresses past the guides 56, 58 into the device.

FIGS. 2A through 2D also show a pair of tube holders 70, 72 aligned with guides 56, 58 in the housing 12. FIGS. 3A and 3B show an enlarged view of another tube holder 70 of the present invention. As shown in FIGS. 2A through 2D and 3A and 3B, each tube holder 70, 72 has a first part 74, 76 and a second part 78, 80, respectively. Each first and second part 74, 76 and 78, 80 has a recess or groove 82, 84 that corresponds with an outer diameter B of the tubing 50. The first part 74, 78 is movably attached to the second part 76, 80 via a hinge 85 or similar mechanism. When the tube holders 70, 72 are in the closed position, an aperture 90 is formed extending through the holder 70, 72. A diameter C of this aperture 90 is slightly smaller than the outer diameter B of the tube 50. In this way, the tubing 50 is fed through the guides 56, 58 and received in the tube holders 70, 72. In an embodiment, an inside surface of the tube holders 70, 72 is tapered (not shown). The aperture 90 may be slightly tapered toward the center of the device 10. In this example, the diameter C of the aperture 90 facing the inside of the device is smaller than a diameter of the aperture facing the guides 70, 72. When in the closed position, the tube holders 70, 72 close with sufficient force to grip, but not flatten, the tubing. In addition, if necessary, the aperture 90 uniformly compresses the tubing 50 and forces the tubing to maintain a cylindrical shape. This may be necessary if, for example, the tubing 50 is not cylindrical due to storage conditions of the tubing or prior sterilization methods, e.g., steam sterilization or ETO sterilization, which may cause the tubing 50 to coil and not be perfectly round.

In an embodiment, the tube holders 70, 72 are mounted on a bar 100. Each tube holder has a guide arm 102, 104 associated with it. The guide arms 102, 104 extend below the bar 100 to a track 105 in a plate 106. As described in more detail below in conjunction with FIGS. 4A through 4H, the plate 106 moves back and forth within the housing 12. As the plate 106 moves to the back 16, the tube holders 70, 72 move in a straight line toward each other to the center of the device 10 (See FIGS. 4D and 4E). The guide arms 102, 104 may be, for example, a lead screw or lever/cam/slot mechanism or a combination of any of these. With the assistance of the guide arms 102, 104, the tube holders 70, 72 pull or push the tube 50 within the housing 12; thus, manipulating the tubing 50 to a desired position, e.g., sterilizing and opening two sealed ends of tubing, and connecting the two ends together, or disconnecting, sterilizing and sealing the ends of a single tube.

As will be described in detail below, the device 10 also includes a hammer 110 and an anvil 112. The hammer 110 and anvil 112 are used during the disconnecting process of the tubing 50. The hammer 110 is movably mounted to a motor 114 via a shaft 116. In an embodiment, the hammer 110 moves forward and backward along the shaft 116 in the housing. As the hammer moves forward, a front part 111 of the hammer contacts a surface 113 of the anvil 112. The hammer 110 may be made from a metal, ceramic, or even rigid plastic material.

Laser Optics

The device also includes a laser unit 200. In a preferred embodiment, the laser unit 200 is a semiconductor diode laser which can be a single laser diode or a laser array of diodes. However, other types of lasers can be used in the invention. For example, Argon, $CO_2$ or YAG lasers may be used. The laser characteristics, e.g., wavelength of the laser, should be evaluated to determine the corresponding characteristics of the tubing 50 to be used in the application. In an embodiment, the laser unit 200 may have an optical assembly to direct a controlled laser beam to the desired location for the connecting or disconnecting processes.

FIGS. 2A through 2D and 4A through 4H show an optical assembly 202 according to an embodiment of the invention. In this example, the optical assembly 202 includes a collimator 204, and a reflective prism 206. Depending on the characteristics of the laser unit 200, a laser beam may begin to diverge as soon as it leaves the unit 200. In this scenario, the collimator 204 limits the divergence of the laser beam. Specifically, the collimator 204 has a generally flat back surface 207 that faces the laser 200. The collimator 204 also has slightly convex front surface 208. As the laser energy travels through the collimator 204, the collimator refocuses the laser beam to the prism 206. Other applications, for example $CO_2$, may have a small laser beam that can be expanded by using a beam expander. The collimator 204 is, preferably, made from an acrylic material, however, other transparent or translucent materials may be used.

The prism 206 splits the laser beam and directs the split beam to the desired location, e.g., the tube ends 51, for the connection process. In order to obtain optimal laser concentration during the connection process, the design of the prism 206 is directly related to the prism location in the device 10. In a preferred embodiment, the prism 206 is between the two tube holders 70, 72. In this example, the prism 206 is constructed from two plano convex lenses 210, 212 juxtaposed to each other.

As is further described below, the prism 206 may also include a light pipe 220 that intersects a center 222 of the prism 206. The light pipe 220 directs the laser beam during both the connecting and disconnecting processes. In addition, the anvil 112 is along a back 224 of the prism lens 206 and, specifically, near an end 230 of the light pipe 220.

Tubing

In general, the material of the tubing 50 is a flexible plastic. In a preferred embodiment, the material is a thermoplastic, kraton polypropylene blend, or the like. In one preferred form of the invention a chemical additive is added that is responsive to the laser to generate heat. One particularly suitable additive can be selected from dyes. The dye is selected to absorb energy at or near the wavelength of the laser diode to promote absorption of the energy of the laser, thereby heating the tubing. Thus, the frequency of the laser selected, e.g., semiconductor diode or YAG laser, should match the specific characteristics of the dye that is added to the tube material. In some applications, e.g., $CO_2$ laser applications, no dye may be required because the absorption wavelength of the tube is the same as the wavelength generated by the laser.

Moreover, a second dye may be added to color code each of the tubes. Such color coding creates a machine detectable and patient detectable distinction between the tubing that is connected to the patient and the new tubing to be connected. For example, the catheter tubing that is implanted in the patient, or the transfer set connected to the catheter, may be dyed one color and the tubing that is attached to the bag of fluid may be dyed a different color. This color distinction is especially helpful for patients that are visually impaired. Other methods of distinction may be employed without departing from the spirit of the invention.

Sensors

A number of sensors 300, 302, 304, . . . are positioned within the housing 12. It should be understood that the location of the sensors identified in the drawings is just one example. Other acceptable locations for the sensors may be accomplished depending on the layout of the components within the device 10. These sensors detect and confirm different stages of the process, whether it is during the connection or the disconnection processes. For example, during the connection process, a sensor 300 may be employed to identify an object at the funneled pathway 52, 54. If the object is acceptable, e.g., the tubing 50, the sensor 300 will activate the guides 56, 58. If the object is not acceptable, the guides are not activated. Thus, these sensors help to keep out foreign objects, and even fingers. This sensor 300 may be, for example, an absorption sensor. An absorption sensor identifies tubing 50 that has a dye. In this way, not only will the sensor keep out foreign objects but also it will identify if improper tubing is attempting to be loaded. As mentioned above, the patient's catheter (or transfer set connected to the catheter) may be a different color than the tube connected to the fluid or blood to be administered to the patient. In this way, the absorption sensor checks to make sure the patient-side and disposable (or bag-side) sealed end tubes are loaded in the pathways 52, 54. If the user attempts to improperly load two bag-side tubes, the sensor 300 alerts the user and the user must retry the loading procedure. Depending on the application, the sensor may be set to allow certain combinations of tubing to enter the apparatus. Thus, the sensor 300 provides a safety measure to guard against improper loading.

Another sensor that may be used in the device 10 is an edge sensor 302. The edge sensor 302 identifies when tube ends 51 extend beyond the tube holders 70, 72 during loading of the tube ends 51 into the device. Specifically, as the tube end 51 crosses the light beam path, the signal from the photo detector 302 is fed into a comparator. The sensor 302 subsequently switches the output state at the desired threshold level, e.g., when sufficient tube length extends beyond the tube holder 70, 72. The sensor 302 may be, for example, a precision edge sensor such as a Cartesian Ovoid LED and a die mounted aperture photo detector. However, other sensing devices capable of identifying the edge of the tube 50 may be used.

Moreover, during the disconnection process, the single tube is loaded into the device for sealing and separation. A color sensor 300 or 304 checks to make sure that not all the tubing in the device is the same color. If the entire tube 50 is the same color, the device will not be able to locate the prior weld. The sensor 304 alerts the user and the patient must reload the tube 50 and try again. This occurs because the sensor 304 also determines where to disconnect the tube 50 based on the position of an existing weld W in the tube. Therefore, when two tubes of different color are present at the sensors 304 the existing weld W is somewhere in between.

After the sensors confirm the tubing 50 is loaded properly, the same or different sensor 304 determines the location of the existing weld W in the tube. This may be accomplished, for example, using a digital camera—like mechanism that searches for the flange in the weld. In a preferred embodiment, the sensor 304 is a CMOS Image Detector. Once the existing weld W is located, the sensor identifies the position for crimping, sealing and separating the tube. The sensor then activates the guides and moves the tube a predetermined distance, on the catheter side, toward the patient. For example, the existing weld may be located at position X. The sensor locates the weld and moves the tube X+⅛" toward the patient side for the location of the cut. In this way, the sensor ensures that the section of tube containing the existing weld W is discarded. This maintains the integrity of the remaining tube in the transfer set that leads to the catheter tube implanted in the patient. In addition, the sensor provides a safety measure since making a new weld on top of an existing weld may not be sufficiently durable.

As described in further detail below, the device 10 also includes a number of temperature or heat sensors (320) to maintain consistency throughout the operation of the device. These sensors 320 may be infrared sensors, such as thermopile infrared sensors. However, other sensors such as thermal couplers or thermistors may be employed. The sensors 320 are used, for example, during the connection and disconnection processes. The sensors verify the tubing is heating properly and may be calibrated to indicate a level of heat is reached for a "good weld" or "bad weld." For example, in applications where the tubing includes a dye, the heat is absorbed by the dye and, in turn, the tubing begins to melt and flow. In this way, the sensors are non-contact temperature sensors that correspond to the infrared output of the tubing as the tubing absorbs the energy from the laser.

Thus, sensors may be employed to compensate the effectiveness of the system based on efficiency of the dye concentration of the tubing, power variation, or laser optic variations.

The Method

Figure 2A:
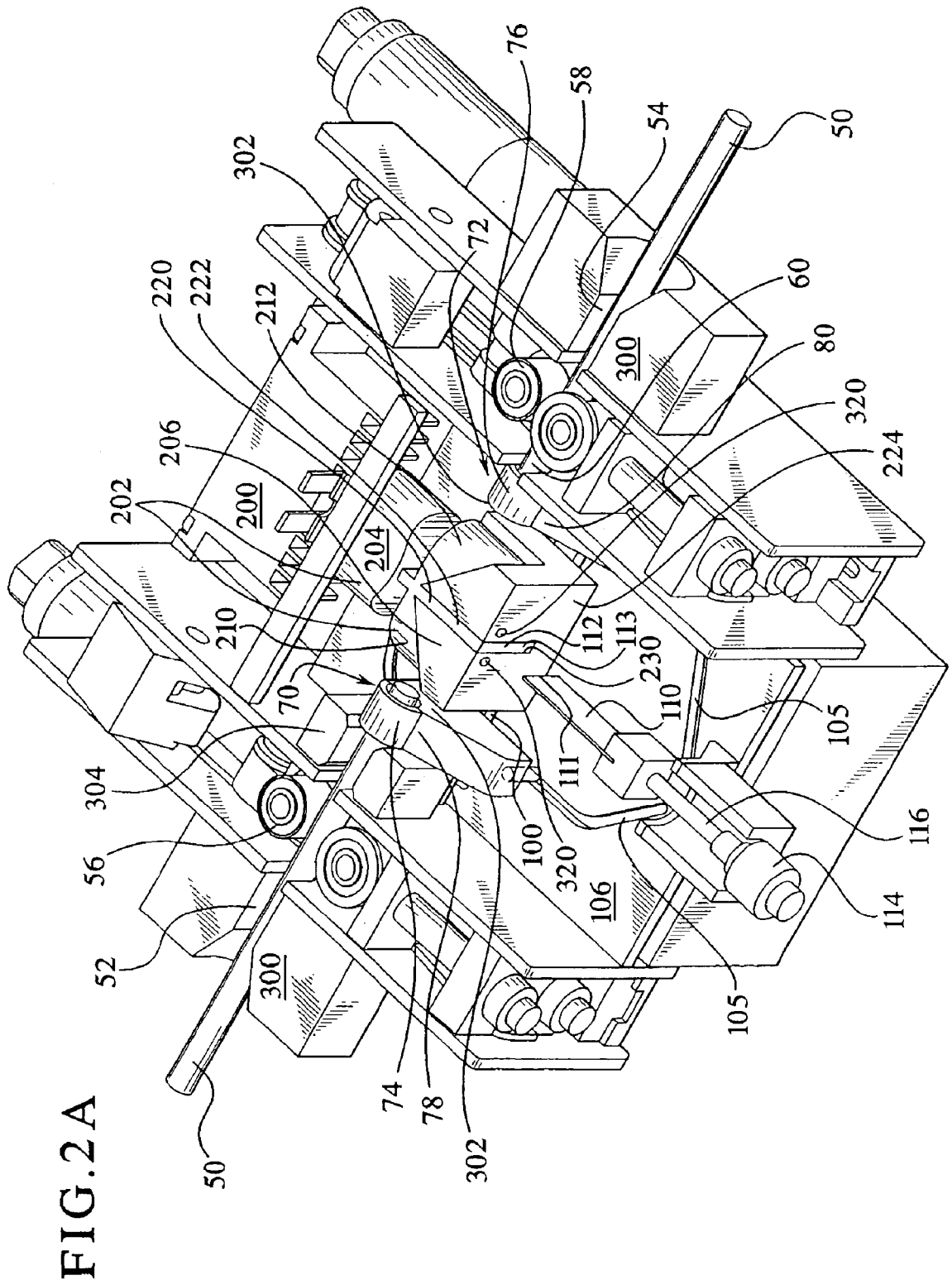
FIGS. 2A through 2D illustrate a perspective view of a connection and disconnection device according to principles of the present invention.
Figure 2B:
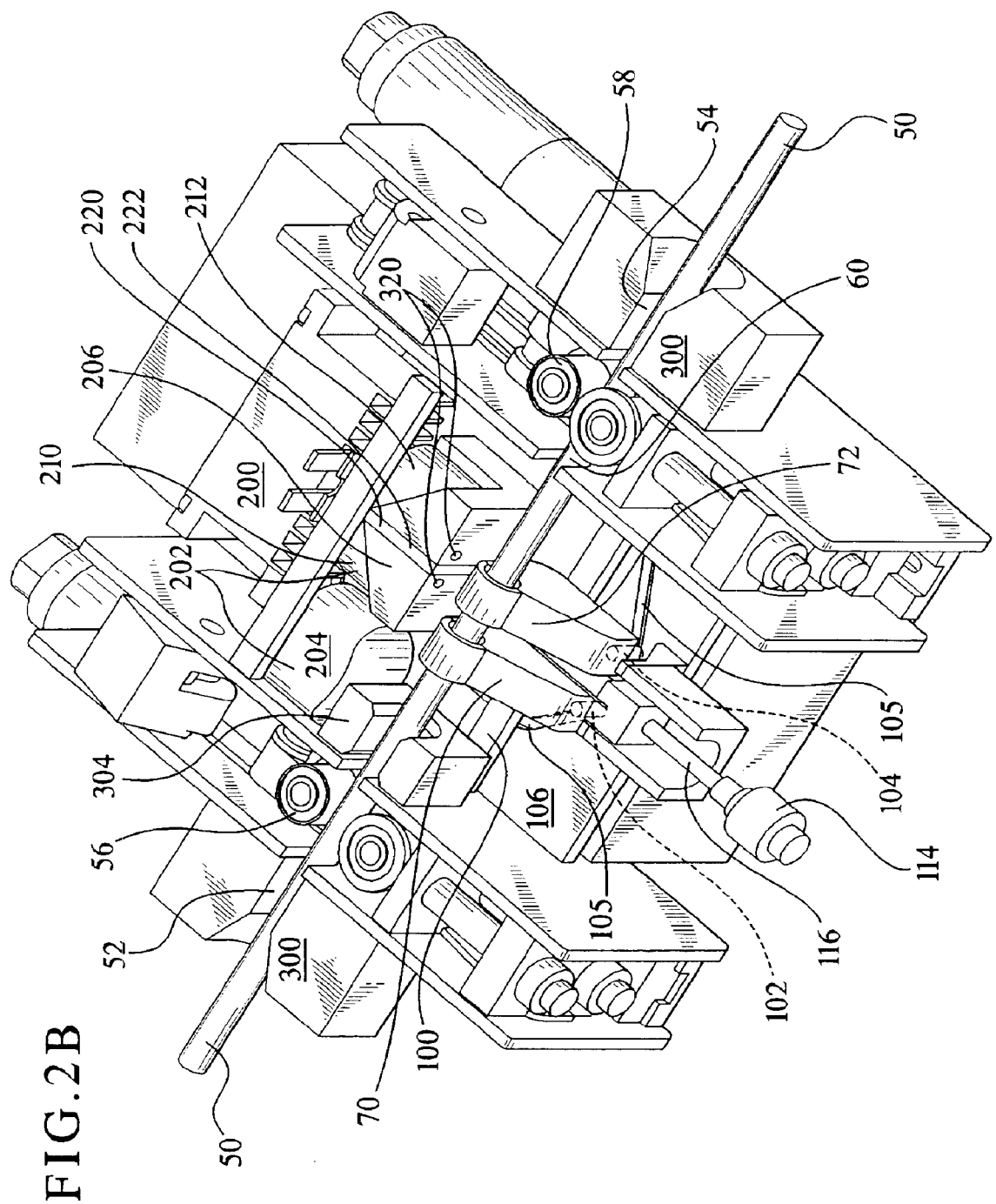
Figure 2C:
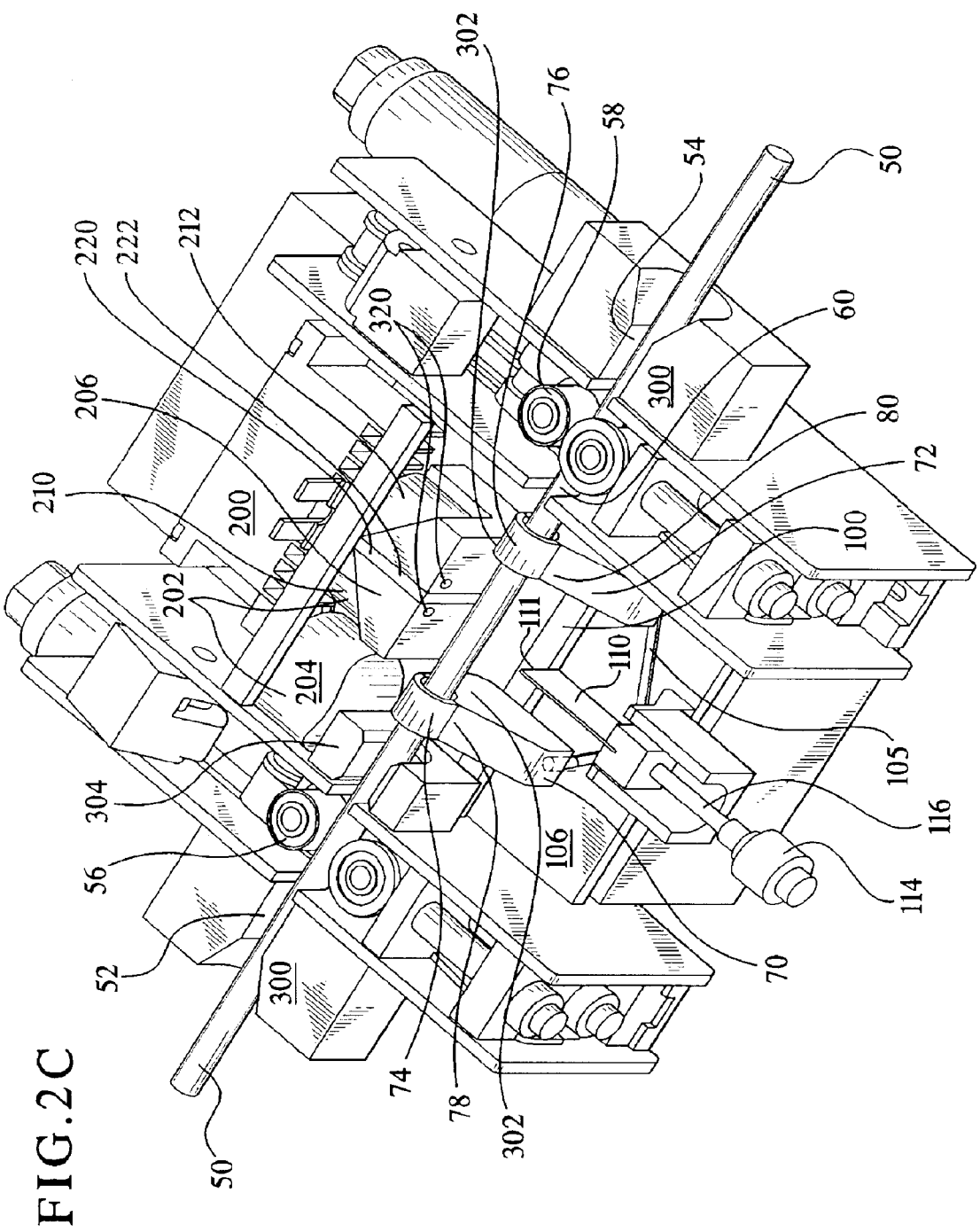
Figure 2D:
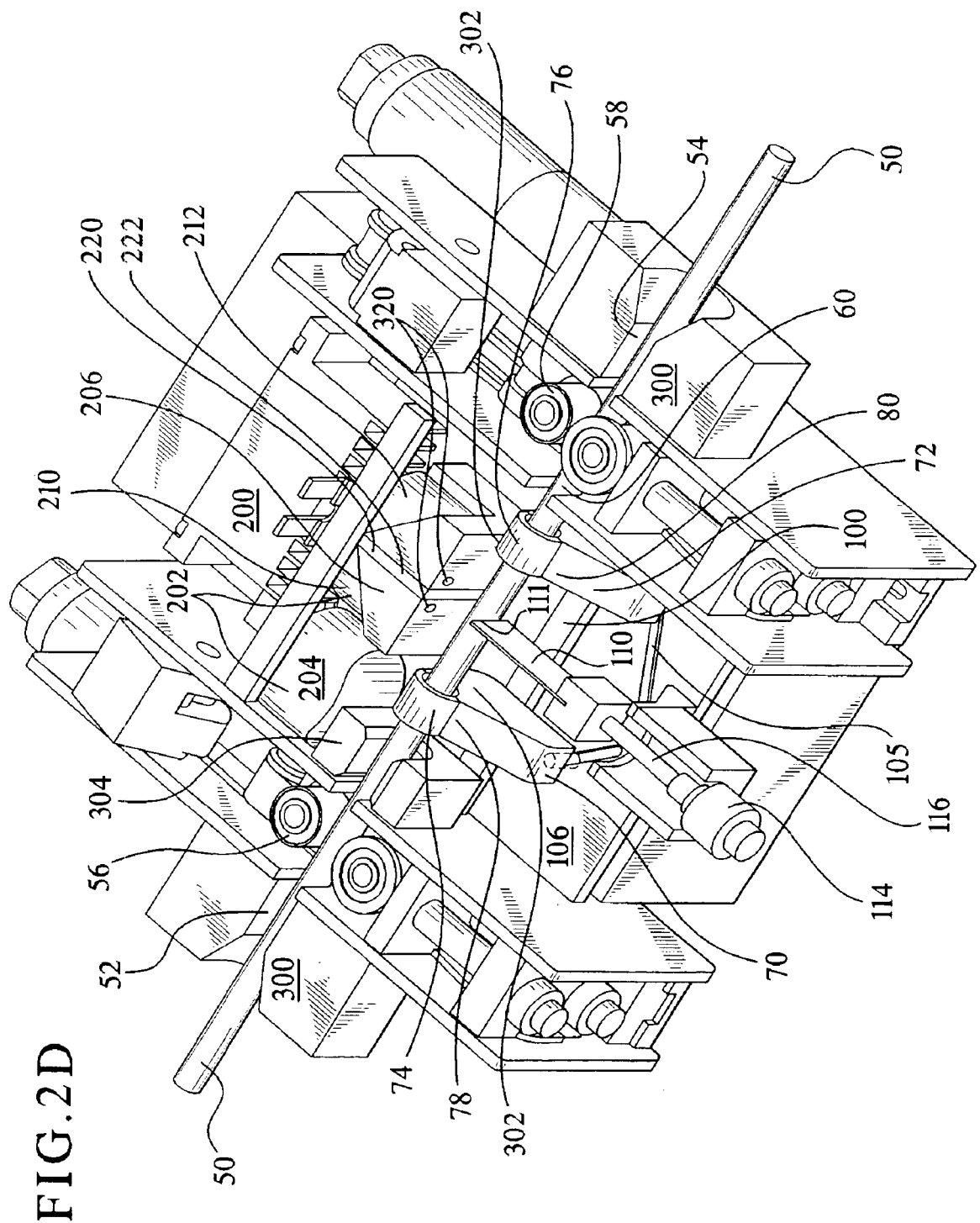
Figure 3A:
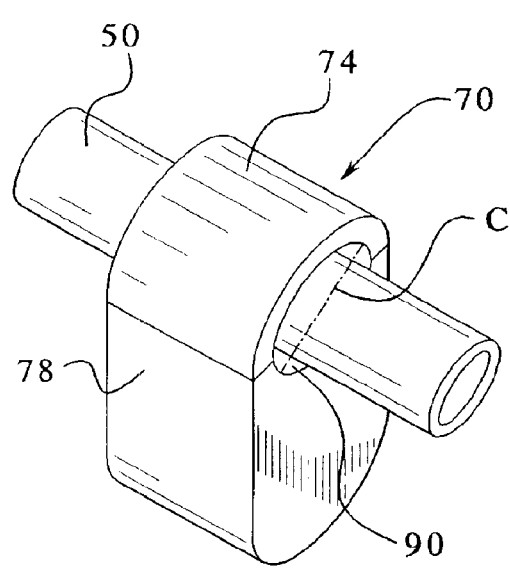
FIGS. 3A and 3B illustrate a perspective view of another tube holder of an embodiment of the present invention.
Figure 3B:
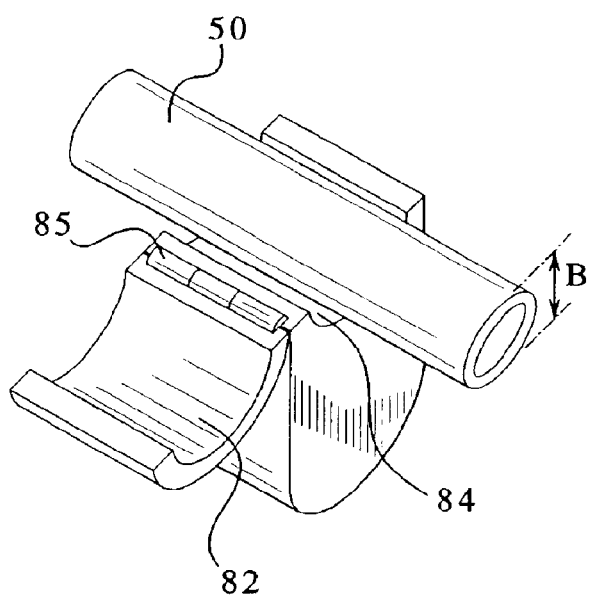

FIGS. 2A through 2D illustrate the connecting and disconnecting process as follows. Specifically, FIGS. 2A and 2B show the inventive process that connects two tube ends together. FIGS. 2C and 2D show the inventive process that disconnects the tubing. Additionally, FIGS. 4A through 4H show a simplified schematic of the connecting process.

Method of Connecting Two Tube Ends

The method of connecting two tube ends will now be described. During the connection process, the lid 24 is closed. As shown in FIGS. 1, 2A, 4A and 4B, the user inserts two tubes 50, each having a sealed end 51, into the device 10 via the loading area openings 30, 32, 38, 40. However, it is within the scope of the invention to use at least one tube end 51 that is not sealed, but, open. In applications involving an open tube end, several types of end caps may be used to maintain the necessary sanitation levels at the inside of the tube. One type of end cap may be a sealed "drum head" that covers the end of the tube. The sealed "drum head" may be a piece of film placed over the open end of the tube and sealed around the entire face of the tube. Another example may include an open end with a vented seal over the face of the tube. A vented seal may be, for example, a perforated membrane. In this example, an end cap would be added to cover the vented end for sanitation purposes.

Figure 4A:
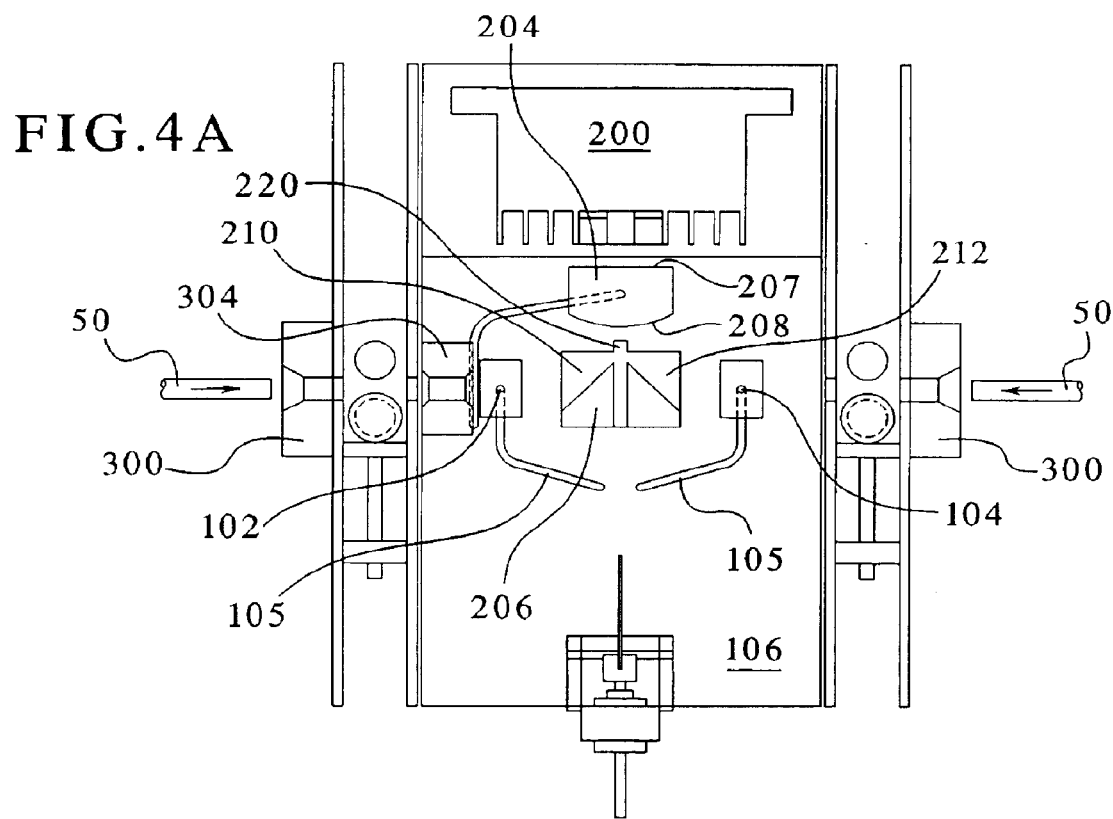
FIGS. 4A through 4H illustrate a schematic plan view of the embodiment in FIGS. 2A through 2D.
Figure 4B:
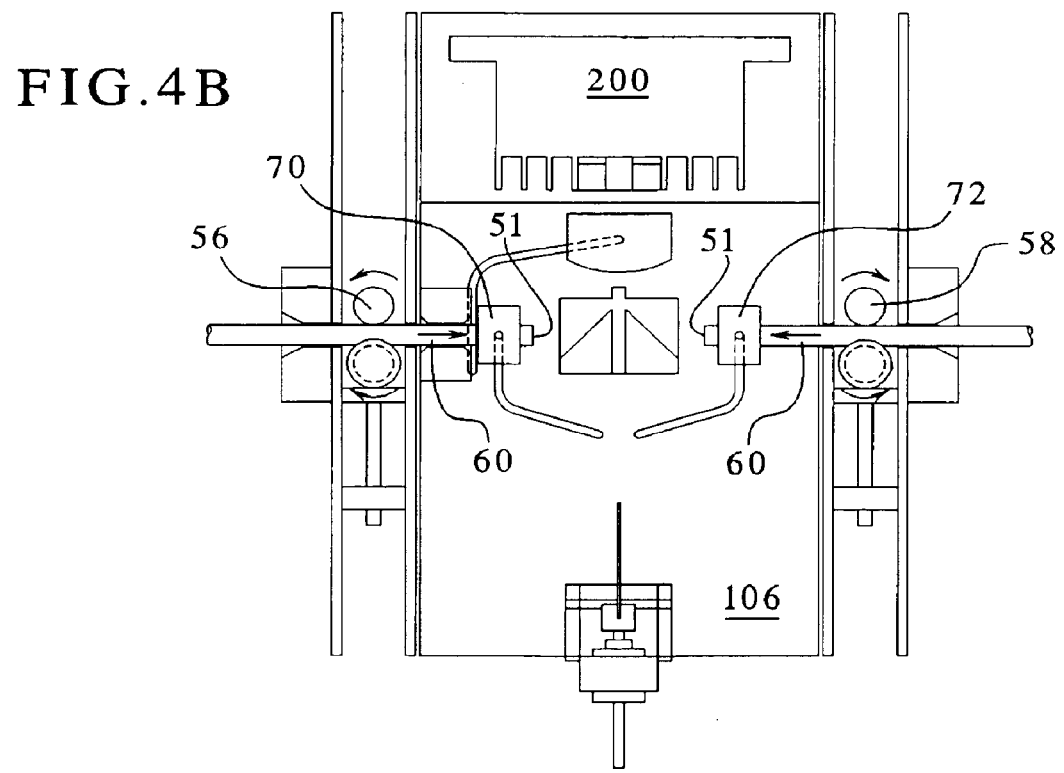

As each tube end 51 enters a respective passageway 52, 54 the sensor 300 identifies the tubing 50 and checks to make sure that one tube end 51 is the patient's tube and the other tube end 51 is the bag tube. It should be noted that it does not matter which tube is loaded into which loading area. Advantageously, the sensors 300 at the passageway 52, 54 communicate with each other to determine that one of each tubing type is loaded. When the tubing is properly loaded, the guides 56, 58 are activated. (FIG. 4B). The guides 56, 58 crimp or squish the tubing and advance each tube end 51 into the device 10 to the tube holders 70, 72. This crimping or squishing creates a vacuum effect in the tubing and purges fluid from the portion 60 of tubing that enters the device 10. The precision edge sensor 302 identifies when the tube 51 extends the predetermined length beyond the holder 70, 72 and stops the guides 56, 58.

Figure 4C:
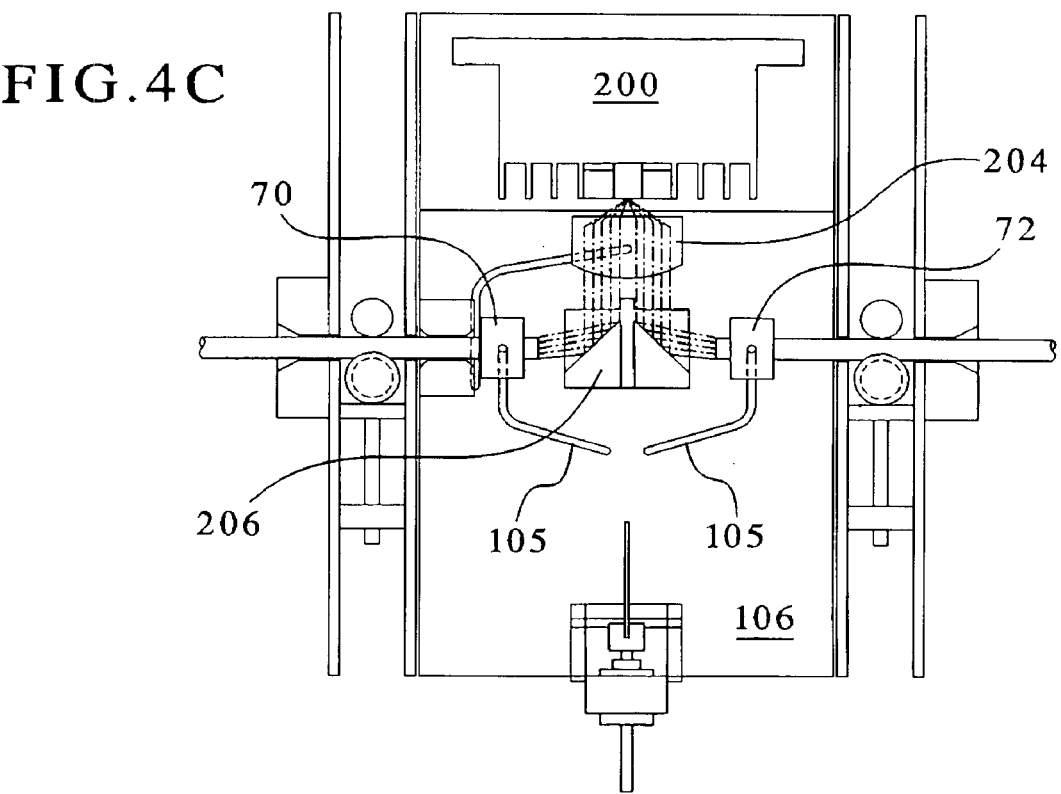

In FIG. 4C, the reflective prism 206 is between the tube holders 70, 72 After each tube end 51 is loaded into its respective tube holder 70, 72, the laser unit 200 is activated and energy diverges from the laser source. The collimator 204 refocuses the diverging energy toward the prism lens 206. As the energy/light strikes the reflective prism 206 it reflects into two bundles of energy. In this embodiment, the prism lenses 210, 212 re-direct each bundle of energy at approximately a 90 degree angle to focus the energy around the tube ends 51. More particularly, a "spot" of energy strikes the tube ends 51 and preferably, slightly exceeds the diameter B of the tube 50 to ensure the tube is covered with adequate radiant energy.

Heat sensors 320 positioned in the housing 12 detect the temperature near the sealed ends 51. Such heat sensors 320 may be, for example, thermopile infrared sensors. As the laser beam strikes the sealed tube ends 51, the heating, melting and aseptic (and/or sterilization) process begins. Depending on the application, the sensors can be used to detect the desired temperature levels for melting and welding. For example, some applications require aseptic conditions be generated. Typically, aseptic, high level disinfection, or germicidal conditions include a less than 6 log reduction of heat resistant spores. Other applications may require sterile conditions be generated. Sterile conditions generally include an operating mode of equal to or greater than a 6 log reduction of heat resistant spores.

As the temperature of the tubing material at the tube ends 51 increases, the tube ends 51 begin to melt, flow and reopen. The tubing material has a certain level of "memory"—as the sealed end of the tube reopens, the tube is predisposed to returning to its symmetrical, circular form. FIGS. 5A and 5B illustrate an example of the laser beam striking the sealed tube end 51. As the laser beam strikes the tube end the rise in temperature at the tube end causes the sealed end to peel open and flare. Once the heat sensors 320 detect that the required aseptic or sterilization temperature level is obtained and sufficient melting of the tube ends 51 has occurred the laser 200 shuts off.

Figure 4D:
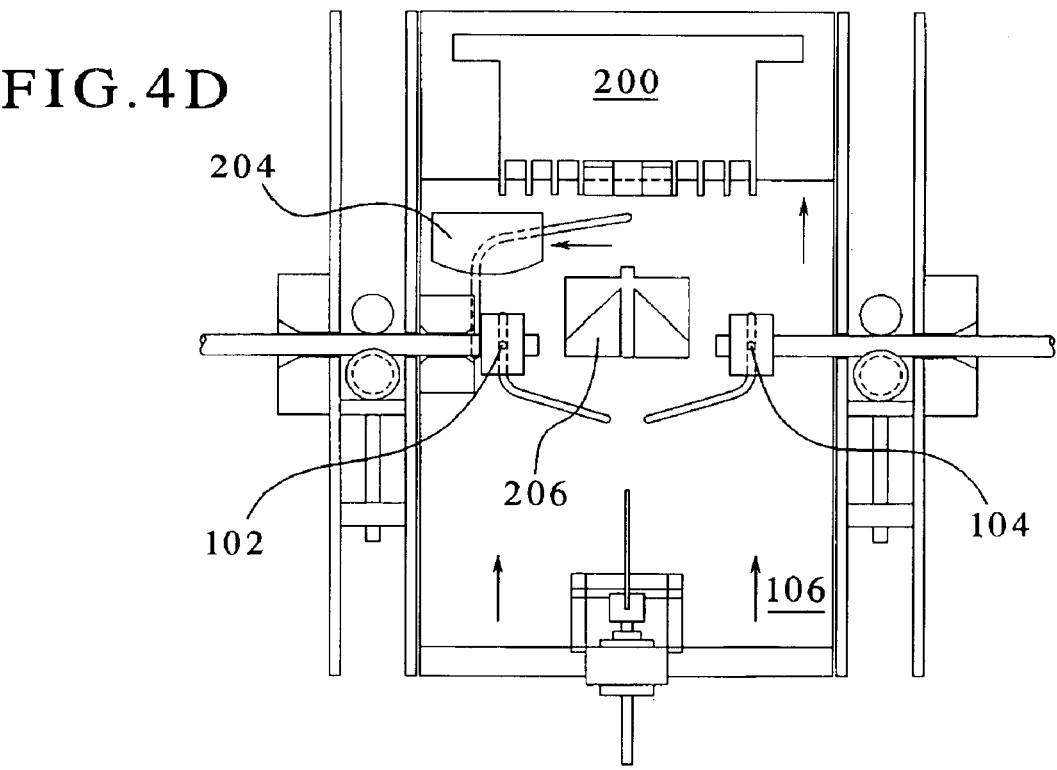
Figure 4E:
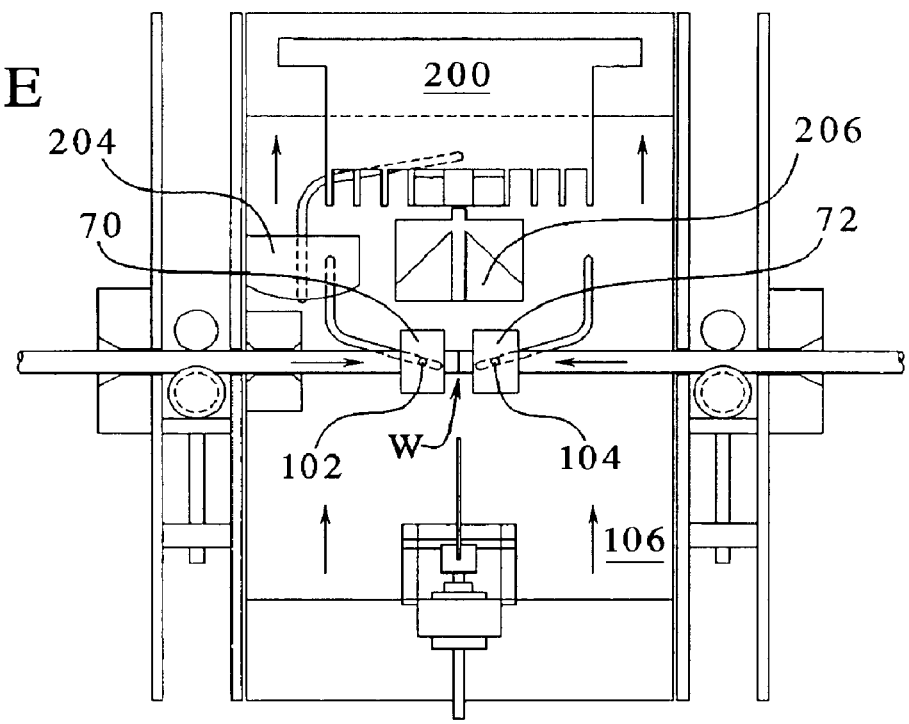
Figure 4F:
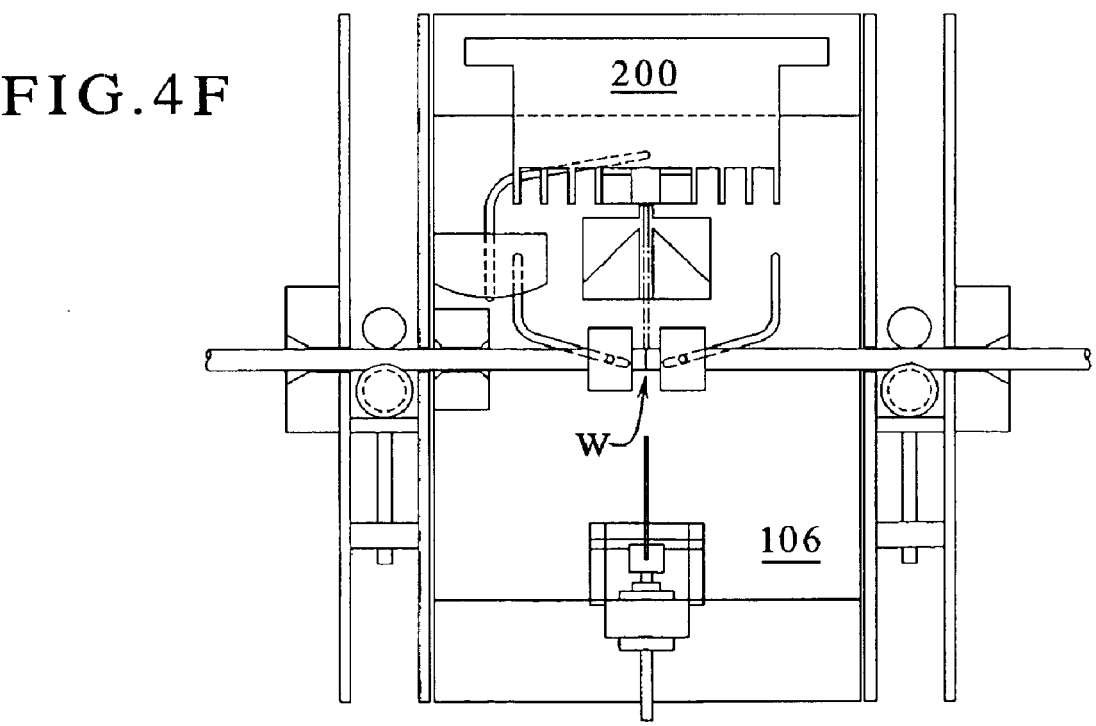

FIGS. 4D through 4F show the next step of the connecting process. After the laser 200 shuts off, the plate 106 moves to the back 16 of the housing 12. As the plate 106 moves, the collimator 204 moves to the side 18 along track 107. At the same time, the prism 206 moves toward the laser unit 200, and the tube holders 70, 72 come together via track 105. At this point, the now melted and aseptically heated or sterilized tube ends 51 contact each other. A weld-seal W is formed. Typically, the weld W is in the form of a ring as shown in FIG. 5C. The tube holders 70, 72 remain in this position until the weld W has sufficiently cooled. In another embodiment, the laser unit 200 may be energized again (FIG. 4F). As shown in FIG. 4F, the laser beam is directed down the light pipe 220 to the tube ends. In this example, the weld-seal W forms and the laser unit 200 is shut off. In an embodiment, the weld-seal W is a hermetic seal.

In applications that use at least one "drum head" end, this type of end responds to the laser in a similar manner as that described above regarding the opening of a sealed end tube. One example of the "drum head" end is as follows. The film of the "drum head" may have a higher concentration of dye than the tubing material. Thus, the film heats faster than the tubing material. The film melts and flows outward to the perimeter of the tube and combines with the tube. The film material may be made from a variety of polymer materials such as polyolefins, polyamides, polyesters, styrene and hydrocarbon copolymers and particularly block copolymers of styrene and dienes and their hydrogenated derivatives, ethylene and vinyl acetate copolymers, ethylene and methacrylic acid copolymers and their ester derivatives. The film may be made from a blend of these materials and can be a monolayer or multiple layer structure. For example, polypropylene, polypropylene-Kraton blend, polypropylene polyethylene blend, or other compatible material.

Other embodiments may include one tube holder that is stationary and one tube holder that moves within the apparatus.

Weld Inspection Process

Figure 4G:
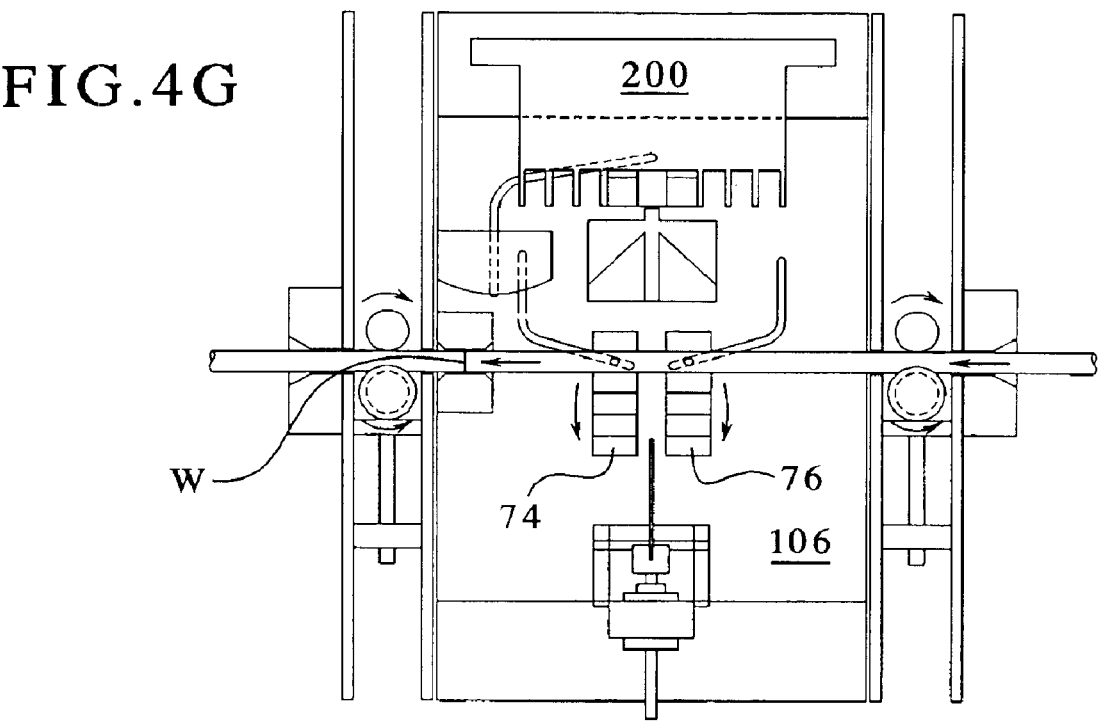
Figure 4H:
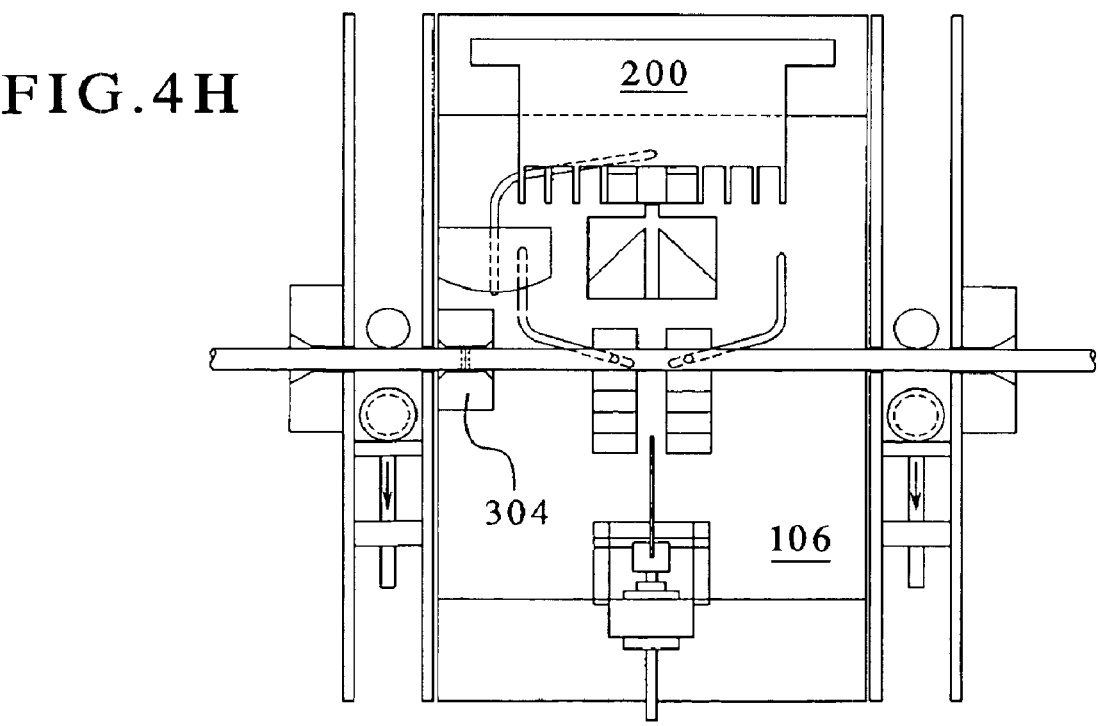

FIGS. 4G and 4H show the weld inspection process. Upon cooling, the first part 74, 78 of the tube holders 70, 72 open and the guides 56, 58 move weld W to the weld detecting sensor 304 for the post process inspection. The inspection process analyzes, for example, the weld thickness and weld height. This data is compared to the profile data for an acceptable or "good" weld. In a preferred embodiment, this sensor 304 is a CMOS image sensor. However, other similar image sensors may be employed. If the post process inspection indicates that the weld is a "good" weld, the lid 24 is unlocked and the guides 56, 58 open. The user is free to open the lid 24 and remove the connected tubing.

On the other hand, if the post inspection process indicates a "bad" weld, the device automatically pinch seals the patient-side of the tubing. The automatic pinch seal process reduces the possibility of contaminants entering the tubing. During this situation, the user is notified of the "bad" weld. The user can then obtain another bag-side tube and start the connection process again. This unique inspection process provides a safety feature to ensure the patient uses "good" welds only. This is especially helpful for visually impaired patients who may have difficulty visually inspecting a weld after the connection process.

Method of Disconnecting a Tube

FIGS. 2C and 2D generally illustrate the inventive method for disconnecting and sealing the tube 50. When the user desires to disconnect from the dialysate solution bag, drainage bag, blood bag, or the like, he/she opens the lid 24 of the device 10. When the lid 24 opens, the guides 56, 58 automatically move to the open position. (FIG. 2C, Ref. No. 56). The user places the tube 50 in the groove of the second part 78, 80 of the tube holders 70, 72. In this way, the tube 50 extends along the funneled passageway 52, 54. In this application, it is not necessary for the first part 74, 78 of the tube holders 70, 72 to close. The user closes the lid 24, thus, closing the guides 56, 58 which, in turn, crimp the tubing 50.

It is preferable to place the tube 50 so that the preexisting weld W is approximately centered between the tube holders 70, 72. Similar to the connecting process, the sensor 300 identifies the tubing 50 and confirms that a patient-side tube is at one of the passageways 52, 54 and the bag-side tube is at the other passageway 52, 54. Thus, the sensor 300 confirms that a preexisting weld exists somewhere there between, e.g., within the device.

After the sensors 300 accept the tubing, the same or different sensor 300 or 304 determines the location of the pre-existing weld W in the tube. This may be accomplished, for example, with a digital camera or similar device. The sensor searches for a flange in the weld W. Alternatively, the sensor 304 may detect a distinction in color between the tubing based on the color coding scheme such as that described above. Accordingly, the sensor 304 could identify a color change at the area surrounding the weld, indicating a weld W exists between the two different colors.

Once the pre-existing weld W is located, the sensor 304 identifies the position for the cut in the tube 50. The guides 56, 58 are activated and the tube 50 moves a predetermined distance, on the catheter side, toward the patient. For example, the existing weld may be located at position X. The sensor 304 locates the weld and moves the tube X+⅛" away from the patient side for the location of the crimping and separation of the tube. In this way, the position for the disconnection is a minimal distance from the existing weld. Therefore, waste of tube material of the patient catheter (or transfer set) is minimized. Alternatively, a patient extension line may be used between the transfer set and the disposable (or bag-side). The use of an extension line will prolong the life of the transfer set because the transfer set will not need to be replaced as often. Instead, the patient extension line is easily replaced by disconnecting the old extension line from the transfer set and connecting a new extension to the transfer set by the methods disclosed herein. Moreover, the sensor 304 ensures that the section of tube containing the existing weld is discarded. This improves the integrity of the remaining catheter tube. In addition, the sensor 304 provides a safety measure since making a weld on top of an existing weld may not be sufficiently durable.

At the start of the disconnecting process the laser unit 200 is off. As shown in FIG. 2D, the hammer 110 moves (via shaft 116) into contact with the tube 50. It should be noted that the hammer 110 is not heated prior to contacting the tube 50. As the hammer 110 contacts the tube 50 it compresses the tube so that the inner surface of the tube is touching. To this extent, the hammer 110 pushes the liquid existing in the tube 50 out of the area to be disconnected.

The laser unit 200 is subsequently activated. The light pipe 220 directs the majority of the laser energy down it onto the tubing 50. The tubing 50 continues to be pinched between the anvil 112 and the hammer 110. In this example, the light pipe 220 is a part of the anvil 112. As the heated tubing is pinched it begins to seal. The heat sensors 320 monitor the temperature near the pinched tubing. The laser unit 200 is shut off. In an embodiment, a sensor 320 is mounted on the hammer 110 near the front 111. In general, the sensor verifies the laser is operating properly. The pinch hammer 110 remains in contact with the tubing while the tube cools. After the cooling of the tubes, the hammer 110 moves back to its original position. The guides 56, 58 are then activated and reverse movement a predetermined distance. This predetermined distance is dependent on the size and material of the flexible tube 50. As the guides 56, 58 reverse, the tubing 50 is pulled apart resulting in two sealed ends. Thus, the combination of the guides 56, 58 and the hammer 110 act as a separator to separate the tubing into two sealed end tubes. The device 10 notifies the user that the lid 24 is unlocked and ready to be opened. The two newly sealed ends of tubing are subsequently unloaded from the device 10. Other applications may include a laser that stays on for the duration or is pulsed on and off while the hammer moves in to pinch the tubing.

Protective Film

Figure 6:
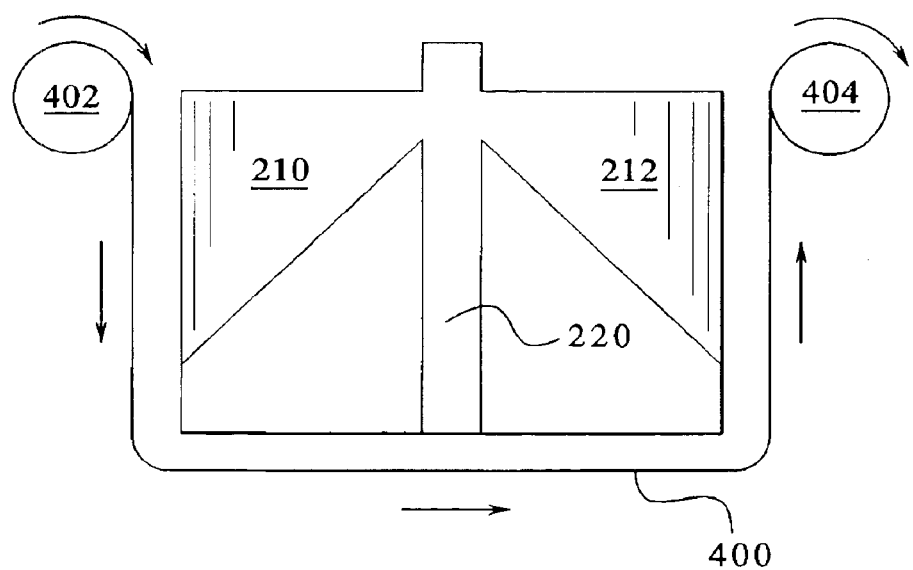
FIG. 6 is a schematic plan view of a protective film according to principles of the present invention.

FIG. 6 shows a protective film 400 according to an embodiment of the invention. The protective film 400 covers the plano convex lenses 210, 212, the anvil 112, and the light pipe 220. The protective film 400 is a thin clear material, preferably, a Mylar® or polyethylene material. The film 400 is provided on, for example, a roll 402 that advances after each disconnection application. When the film 400 advances it is stored in another roll 404. After the roll 402 is used both rolls 402 and 404 can be easily discarded. The laser energy does not have any heating effect on the film. The film 400 does not alter the laser beam characteristics. In this way, the film 400 protects the optics assembly 202 and eliminates cleaning of same. It will be appreciated that one could also achieve this purpose by providing a system of advancing disposable lenses. For example, if the optical assembly includes the light pipe 220 as the anvil 112, the optical assembly could be a number of disposable lenses on a cartridge that rotates after each use. Thus, the used optical assembly is discarded and a new optical assembly is used in each application.

Further Embodiments

Figure 7:
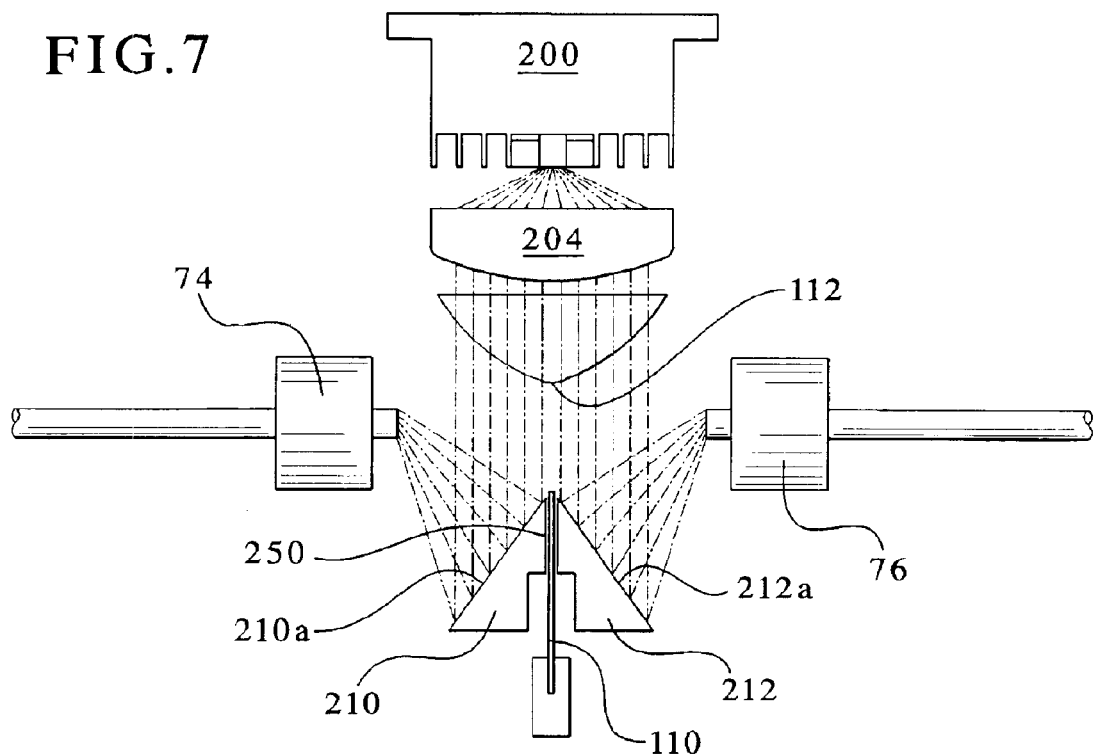
FIG. 7 illustrates a schematic plan view of another embodiment of the present invention.

FIG. 7 illustrates another embodiment of the invention in which the prism 206 and light pipe 220 are not between the tube holders 70, 72 but located near the front 14 of the housing 12. For simplification purposes, FIG. 7 shows the anvil 112 between the collimator 204 and the prism 206. However, during the connection process, the anvil 112 is generally not employed. Instead, the anvil 112 is off to one side 18 or 20 in the housing 12. During the disconnection process, the anvil 112 moves in front of the laser 200. Thus, the anvil 112 may be mounted on a tracing system similar to that-described above with respect to the collimator 204.

During the connection process, the prism lens 206 diffuses the laser beam and spreads the energy over a slightly larger area than that described above in FIGS. 4A through 4H. In this example, the lenses 210, 212 are shown with flat reflecting surfaces 210a, 212a. However, it should be understood that the lenses 210, 212 may be concave or some other configuration depending on the laser type and the need to redirect and focus the beam. Also, the prism 206 may be rough edged lenses 210, 212 to spread the energy at the surface of the sealed tube ends 51. Moreover, another lens (now shown) may be positioned at the surfaces 210a, 212a between the surface and the tubing to further focus the laser beam. As described above with respect to the embodiment in FIGS. 2A and 2B, the tube ends are brought together after the tube ends are sufficiently heated and a weld is formed. However, the embodiment of FIG. 7 is less complex because it is not necessary to move the prism 206 from in between the tube ends prior to bringing the tube ends together.

During the disconnecting process, the anvil 112 moves in front of the laser 200. The hammer 110 moves through a passageway 250 between the two lenses 210, 212 in the direction of the anvil 112. The hammer 110 compresses the tubing 50 against the anvil 112. In this regard, the remaining steps of the disconnection process are substantially the same as that described above.

Figure 8:
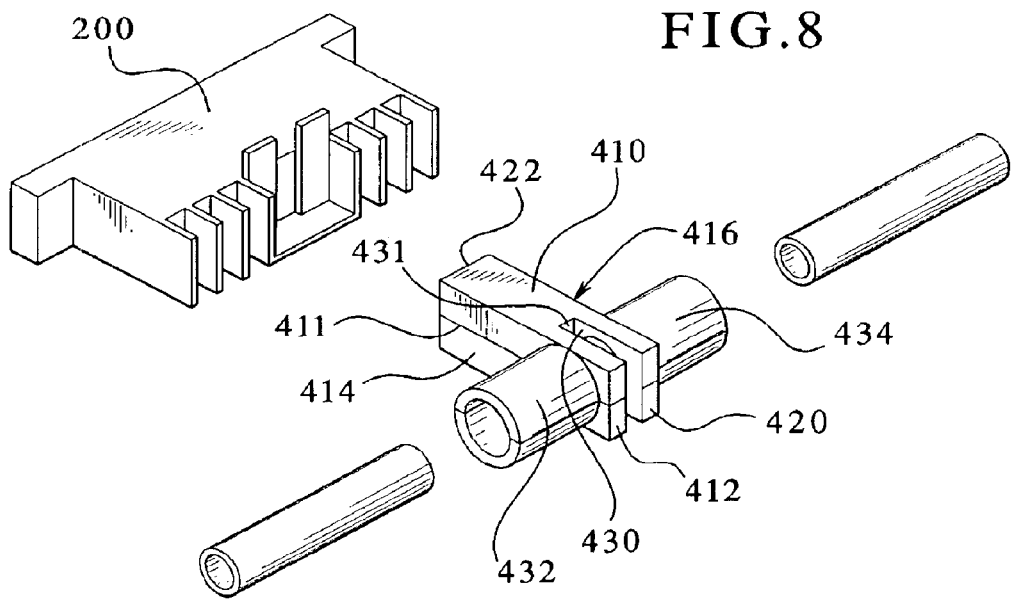
FIG. 8 illustrates a perspective view of an optical assembly of another embodiment of the present invention.

FIG. 8 shows another embodiment of the invention. In this embodiment, the laser optics assembly incorporates a fiber optics assembly 410. The fiber optics assembly can include a large cylinder rod or multiple optical fibers to transmit the electromagnetic energy to the tube and provide the necessary heating and distribution of the energy. In this embodiment, the fiber optics assembly 410 includes a fixed lens 412 with first and second sides 414, 416 and a front and back end 420, 422. A recess or access slot 430 extends from the front end 420 into the assembly 410. The recess 430 ends at wall 431 within the assembly 410. The wall 431 acts as the anvil during the disconnection process. The fiber optics assembly 410 has a parting line 411 in which the assembly may be opened while the tube is loaded for the disconnection process. After the tube 50 is loaded, the recess 430 receives the hammer 110 and the hammer compresses the tube 50 at wall 431. The laser unit 200 is energized and the laser beam is directed down the fixed lens 412 in a similar manner as the light pipe 220 described above. In this way, the crimping and separation process begins.

In addition, a fiber optic member 432, 434 extends perpendicular from each side 414, 416 of the lens 412. During the connection process, the laser unit 200 is energized and the laser beam is directed down the fixed lens 412 to the fiber optic members 432, 434. The fiber optic members 432, 434 emit the laser energy at the tube ends 51. Similar to the embodiment described in FIGS. 2A and 2B above, the assembly 410 moves out from between the tube holders 70, 72 and the tube holders bring the tube ends together to form a weld. If necessary, the laser unit 200 can be energized again and the laser beam is directed down the fixed lens 412 to the area where the tube ends are joined to form a weld.

FIGS. 9A and 9B show another embodiment of the invention. In FIG. 9A, an optical assembly 450 is used with the laser unit 200. The optical assembly 450 is adjacent to the laser unit 200 between the laser unit and a plane X that intersects the tubing 50. The optical assembly 450 includes a generally "Y"-shaped optical splitter 452, in which a base 454 of the "Y" is near the output of the laser unit 200. The "Y"-shaped optical splitter extends from the laser unit 200 toward the plane X. The "Y"-shaped optics may be solid fiber optics or individual fibers.

The optical assembly 450 remains stationary during the connection and disconnection operation of the apparatus.

During the connection of two tube ends 51, the laser beam is split down the "Y" to each tube end. The tube ends are subsequently brought together for welding. During the disconnection process, the laser beam is directed down a center optical component of the assembly or light pipe 456. Similar to the applications described above, the anvil 110 moves toward the light pipe 456 to compress and pinch the tubing. It is also within the scope of the invention to have the optics assembly 450 as two separate components. In this example, the "Y"-shaped optical splitter 452 and the light pipe 456 are discrete components (not shown). Each component 452, 456 is mounted on a movable plane that moves the required component in front of the laser unit depending on the process to be performed by the apparatus.

Figure 10A:
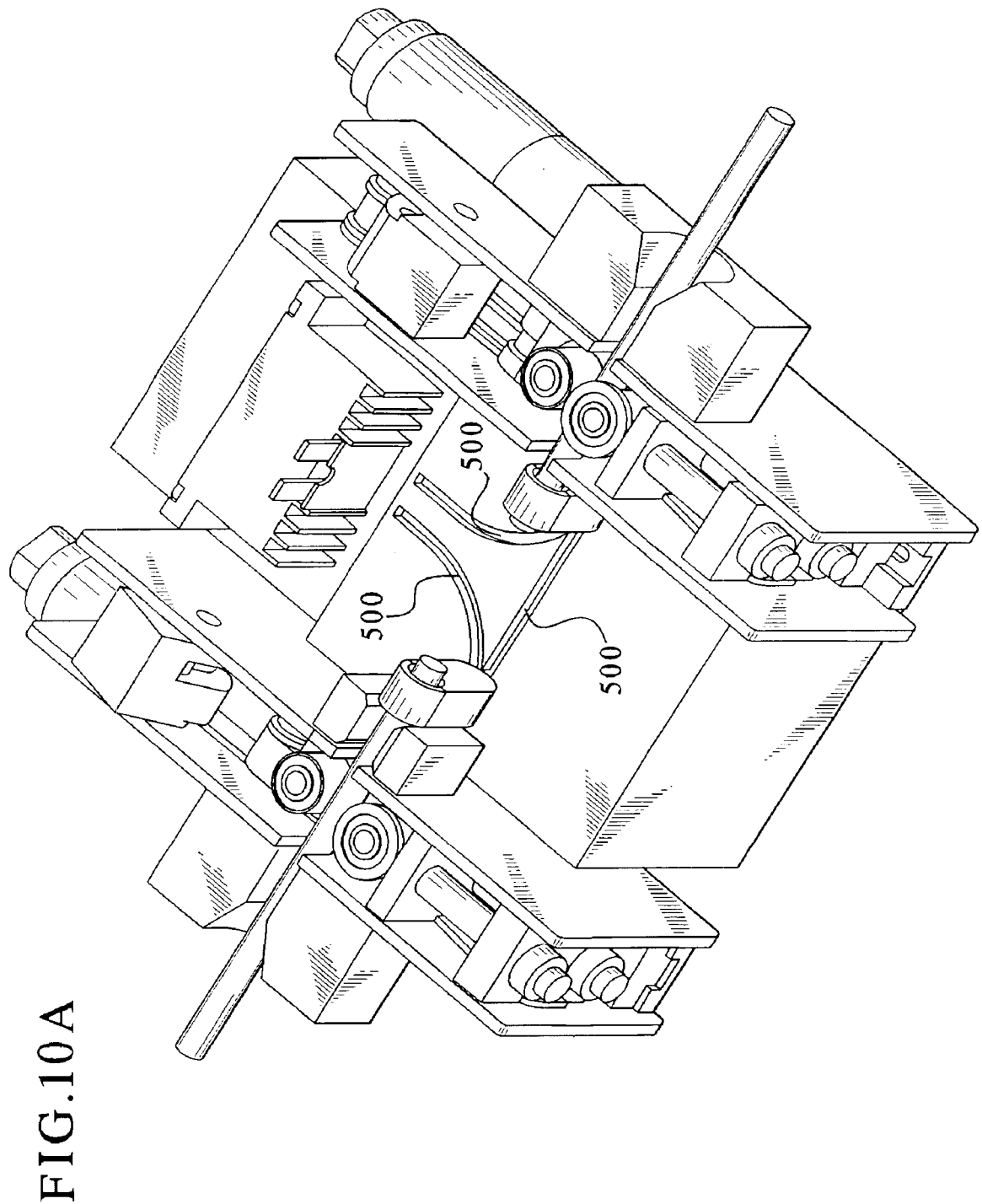
FIGS. 10A and 10B illustrate a perspective view of another embodiment of the present invention.
Figure 10B:
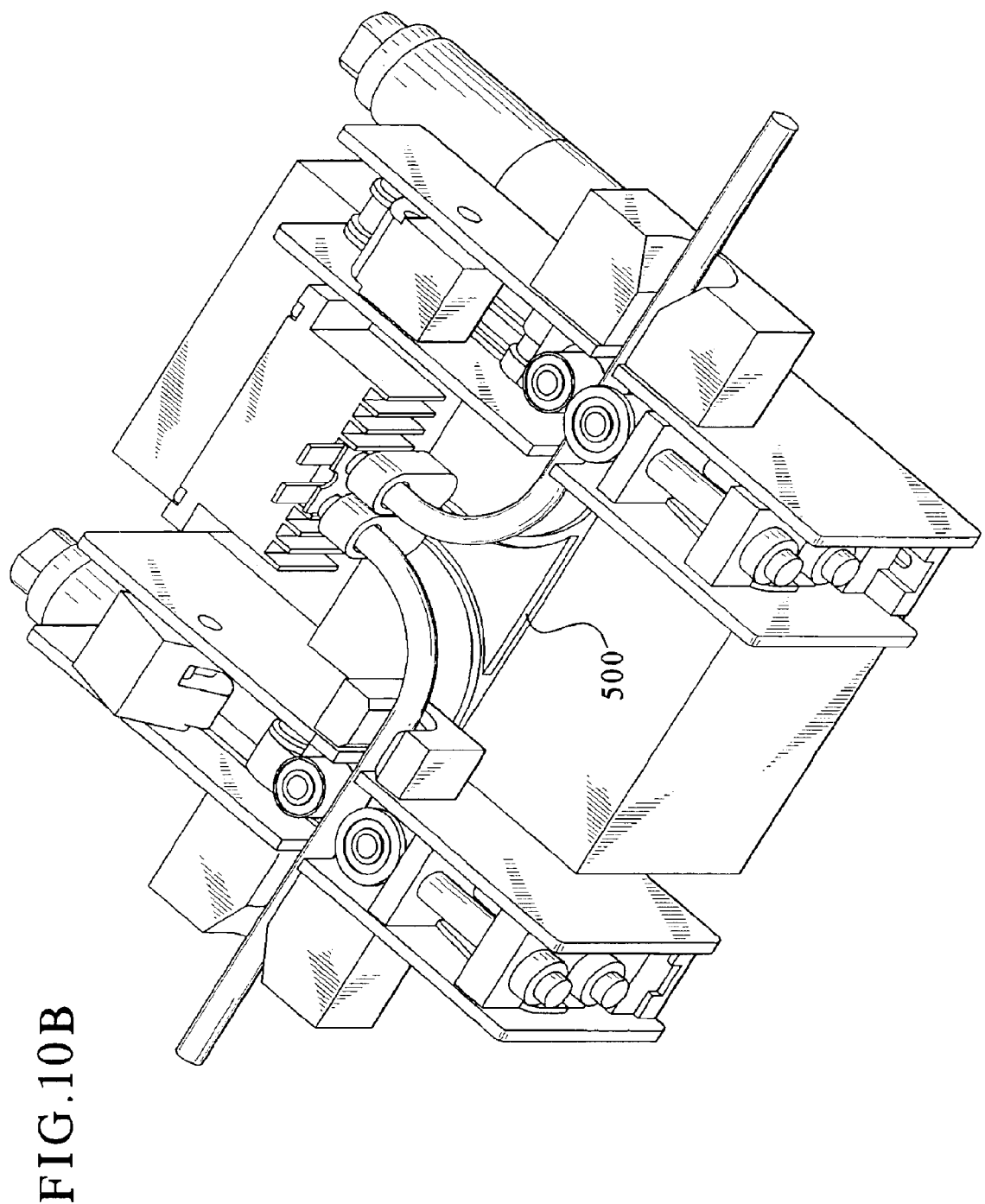

FIGS. 10A and 10B show another embodiment of the invention. In this example, the laser unit 200 is used without the optics assembly. The tube holders 70, 72 are mounted on a track system 500. During the connection process, the track system 500 moves the tube holders 70, 72 along a predetermined path toward the laser unit 200. (FIG. 8B). In this way, the tube holders 70, 72 manipulate the tubes 50 so that the tube ends 51 are, preferably, parallel to each other and face the laser unit 200. Thus, the tube holders 70, 72 rotate approximately 90 degrees from when they receive the tube ends to the point at which the tube ends 51 face the laser unit 200. However, the tube holders may rotate in the range of 70 to 110 degrees and achieve the same results.

The laser unit 200 turns on and melts and sterilizes the tube ends. As discussed above, the tube ends 51 enter the device 10 as sealed tube ends. As such, the tube ends 51 begin to reopen as the laser energy melts this area. The laser unit 200 shuts off once the sensors determine that sufficient heating of the tube ends occurred. At this time, the tube holders 70, 72 retract to their starting position (near guides 56, 58) and then move forward toward each other. The two tube ends 51 come into contact with each other and a weld seal is formed.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A device that provides a connection between two flexible tube ends, the device comprising:
   a laser unit having a laser beam;
   a laser optics assembly capable of changing a direction of the laser beam so that the laser beam strikes the tube ends, wherein the laser optics assembly includes (i) a prism movably mounted between the two tube ends and (ii) a light pipe, the prism operable to reflect the laser beam to heat the tube ends, the light pipe operable to direct the laser beam to weld the tube ends together; and
   a pair of tube holders each adapted to receive a one of the flexible tube ends and adapted to urge the two tube ends together after the two tube ends are aseptically heated via the laser beam, to join the heated tube ends together to form a weld.

2. The device of claim 1, wherein the laser optics assembly includes a collimator, the collimator located between the laser unit and the prism.

3. The device of claim 1, wherein the device includes an apparatus operable to remove the prism from between the tube ends prior to the ends being connected together.

4. The device of claim 1, wherein the laser beam sterilizes the two tube ends.

5. The device of claim 1, wherein the laser optics assembly changes the direction of the laser beam including a plane of the laser beam.

6. The device of claim 1, wherein the laser optics assembly includes a "Y"-shaped optical component adjacent the laser unit, the "Y"-shaped optical component adapted to split the laser beam and direct the laser beam toward each tube end.

7. The device of claim 6, wherein the laser optics assembly further includes a light pipe component.

8. The device of claim 1, wherein the weld is a hermetic seal.

9. The device of claim 1, including a protective film located around the laser optics assembly.

10. The device of claim 1, including a protective film located around the prism.

11. A device for connecting two thermoplastic tube ends together, the device comprising:
    a housing including apertures, each aperture adapted to receive one of the tube ends;
    a pair of guides positioned within the housing to direct the tube ends into the housing;
    two tube holders, each tube holder having an aperture adapted to receive one of the two tube ends;
    a laser unit in spaced relation to the tube holders, the laser unit being capable of projecting a laser beam to the two tube ends to sterilize each end and connect the two tube ends together; and
    a sensor near the tube holders to analyze the connection between the two tube ends.

12. The device of claim 11, further comprising:
    a tracking system connected to the two tube holders and capable of moving the two tube holders together to form a weld between the two tube ends.

13. The device of claim 11, further including an edge detector for sensing the position of each of the two tube ends in the two tube holders.

14. The device of claim 11, further including at least one heat sensor to monitor the temperature near at least one of the two tube ends during the connection process.

15. The device of claim 11, further including an optics assembly to direct the laser beam from the laser unit to the tube ends.

16. The device of claim 11, wherein the sensor is a weld inspection sensor.

17. The device of claim 11, wherein the sensor analyzes a weld characteristic selected from the group of weld thickness and weld height.

18. The device of claim 11, wherein the sensor compares data corresponding to the weld to profile data to determine if an acceptable weld has been formed.

19. The device of claim 11, wherein the sensor is a complentary metal oxide semiconductor image sensor.

20. The device of claim 11, further comprising a hammer and anvil, the hammer operable to pinch the one of the tube ends against the anvil.

21. The device of claim 20, wherein the hammer pinches one of the tube ends against the anvil when the sensor determines that an unacceptable weld has been formed.

22. A device that provides a sterile connection between two flexible tube ends, the device comprising:
    a housing having a back and two slots, each slot adapted to receive one of the flexible tube ends;
    a pair of guides positioned within the housing near each slot, each of the guides directs one of the flexible tube ends into the housing;

a laser unit positioned in the housing;

a pair of tube holders positioned within the housing, each of the pair of tube holders adapted to receive the tube end from one of the pair of guides, the tube holders manipulate the flexible tube ends so that each tube end faces the laser unit for heating, bring the heated tube ends together to form a weld, and subsequently release the resulting welded tube.

23. The device of claim 22, further including a sensor in communication with the guides, the sensor triggers the guides to an "on" state when acceptable tube ends are present in each of the slots.

24. The device of claim 23, wherein acceptable tube ends includes one patient-side tube end and one bag-side tube end.

25. The device of claim 24, wherein the sensor further includes an absorption sensor that identifies tube ends that have a dye.

26. The device of claim 23, wherein the sensor triggers each of the pair of guides to an "off" state when the respective tube end projects a predetermined distance beyond its respective tube holder.

27. The device of claims 22, wherein each of the pair of guides crimps the respective tube end and purges fluid from a portion of the respective tube.

28. The device of claim 22, wherein the pair of guides are pinch rollers.

29. The device of claim 22, wherein the pair of guides are threading devices.

30. The device of claim 22, wherein the laser unit sterilizes the tube ends.

31. The device of claim 22, wherein the laser unit is a semiconductor diode laser.

32. The device of claim 22, wherein the laser unit is an Argon laser.

33. The device of claim 22, wherein the laser unit is a CO2 laser.

34. The device of claim 22, wherein the laser unit is a YAG laser.

35. The device of claim 22, wherein each of the pair of tube holders include an aperture having a diameter that is slightly smaller than an outer diameter of the flexible tube.

36. The device of claim 22, wherein each tube holder has a tracking system to rotate the tube holder within the housing.

37. The device of claim 22, wherein the pair of tube holders are synchronized and move simultaneously to manipulate the two flexible tube ends within the housing.

38. The device of claim 22, further comprising at least one sensor to detect temperature near the tube ends and identify predetermined sterilization levels.

39. A device that provides a connection between two flexible tube ends, the device comprising:

a housing including apertures, each aperture adapted to receive one of the tube ends;

a pair of guides positioned within the housing to direct the tube ends into the housing;

a laser unit having a laser beam;

a pair of tube holders, each adapted to receive a flexible tube end and adapted to urge the two tube ends together after the two tube ends are heated via the laser beam, to join the heated tube ends together to form a weld; and a prism not being positioned between the pair of tube holders, the prism positioned and arranged with respect to the tube ends to direct the laser beam so that the laser beam strikes the tube ends.

40. The device of claim 39, wherein the prism is constructed from two piano convex lenses.

41. The device of claim 39, wherein the prism is constructed from rough edged lenses.

42. The device of claim 39, wherein the prism is constructed from concave lenses.

43. The device of claim 39, which includes an additional lens located between the prism surface and the tube ends, wherein the additional lens further focuses the laser beam at the tube ends.

* * * * *